(12) United States Patent
Bornemann et al.

(10) Patent No.: US 7,166,599 B2
(45) Date of Patent: Jan. 23, 2007

(54) TRISUBSTITUTED PYRIMIDINES

(75) Inventors: Klaus Bornemann, Ingelheim (DE); Hans Briem, Bremen (DE); Cornelia Dorner-Ciossek, Goettingen (DE); Katja Fechteler, Wiesbaden (DE); Klaus Fuchs, Schemmerhofen (DE); Frank Himmelsbach, Mittelbiberach (DE); Klaus Klinder, Oggelshausen (DE); Markus Kostka, Mainz (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/007,923

(22) Filed: Dec. 9, 2004

(65) Prior Publication Data

US 2005/0090486 A1    Apr. 28, 2005

Related U.S. Application Data

(63) Continuation of application No. 10/272,160, filed on Oct. 16, 2002, now abandoned.

(60) Provisional application No. 60/330,128, filed on Oct. 17, 2001.

(51) Int. Cl.
C07D 239/48 (2006.01)
A61K 31/505 (2006.01)

(52) U.S. Cl. .................. 514/235.8; 544/122; 544/323; 544/324; 514/252.14; 514/275

(58) Field of Classification Search ................ 544/122, 544/323, 324; 514/235.8, 275, 252.14
See application file for complete search history.

(56) References Cited

U.S. PATENT DOCUMENTS

| | | |
|---|---|---|
| 5,147,876 A | 9/1992 | Mizuchi et al. |
| 5,703,129 A | 12/1997 | Felsenstein et al. |
| 6,197,779 B1 | 3/2001 | Andries et al. |
| 6,200,977 B1 | 3/2001 | Cushing et al. |
| 6,235,746 B1 | 5/2001 | Davis et al. |
| 6,245,884 B1 | 6/2001 | Hook |
| 6,448,229 B1 | 9/2002 | Teall |
| 6,683,091 B1 | 1/2004 | Asberom et al. |
| 6,713,248 B1 | 3/2004 | Roberts et al. |
| 6,753,410 B1 | 6/2004 | Nadin et al. |
| 6,756,511 B1 | 6/2004 | Castro Pineiro et al. |
| 6,800,477 B1 | 10/2004 | Patel et al. |
| 6,890,956 B1 | 5/2005 | Churcher et al. |
| 2002/0183335 A1 | 12/2002 | Hewawasam et al. |
| 2003/0032647 A1 | 2/2003 | Yamada et al. |
| 2004/0102630 A1 | 5/2004 | Brumby |
| 2004/0224966 A1 | 11/2004 | Brumby |

FOREIGN PATENT DOCUMENTS

| | | |
|---|---|---|
| DE | 40 29 650 A1 | 3/1992 |
| EP | 0 379 806 A2 | 8/1990 |
| EP | 0 945 443 A1 | 9/1999 |
| EP | 1 223 170 A1 | 7/2002 |
| EP | 1 277 741 A1 | 1/2003 |
| JP | 3-127790 | 5/1991 |
| WO | WO 91/18887 | 12/1991 |
| WO | WO 97/19065 | 5/1997 |
| WO | WO 99/41253 | 8/1999 |
| WO | WO 99/50250 | 10/1999 |
| WO | WO 00/12485 | 3/2000 |
| WO | WO 00/12486 | 3/2000 |
| WO | WO 00/27825 | 5/2000 |
| WO | WO 00/27826 | 5/2000 |
| WO | WO 00/39101 | 7/2000 |
| WO | WO 00/53595 | 9/2000 |
| WO | WO 01/19825 A1 | 3/2001 |
| WO | WO 200119825 A1 * | 3/2001 |
| WO | WO 01/55148 A1 | 8/2001 |
| WO | WO 01/64653 | 9/2001 |
| WO | WO 01/64654 | 9/2001 |
| WO | WO 01/64655 | 9/2001 |
| WO | WO 01/64656 | 9/2001 |
| WO | WO 02/04429 A1 | 1/2002 |

(Continued)

OTHER PUBLICATIONS

Jill Murrell, et al. "A Mutation in the Amyloid Precursor Protein Associated with Hereditary Alzheimer's Disease" Science, vol. 25, pp. 97-99, 1991.

(Continued)

Primary Examiner—Kahsay Habte
(74) Attorney, Agent, or Firm—Michael P. Morris; Mary Ellen Devlin; Philip I. Datlow

(57) ABSTRACT

The present invention relates to trisubstituted pyrimidines of formula

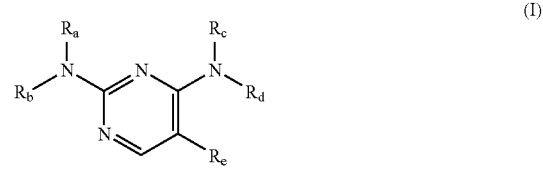

(I)

wherein $R_a$ to $R_e$ are defined as in claim 1, which are suitable for the treatment of illnesses in which β-amyloid modulators have a therapeutic benefit, the use thereof for preparing a pharmaceutical composition with the abovementioned properties, and processes for the preparation thereof.

7 Claims, No Drawings

FOREIGN PATENT DOCUMENTS

| | | |
|---|---|---|
| WO | WO 02/066036 A1 | 8/2002 |
| WO | WO 02/096888 A1 | 12/2002 |

OTHER PUBLICATIONS

Barbara Cordell "B-Amyloid Formation as a Potential Therapeutic Target for Alzheimer's Disease" Annual Review Pharmacology and Toxicology, 1994, 34:69-89.

Marie-Christine Chartier-Harlin, et al. "Early-onset Alzheimer's Disease caused by Mutations at Codon 717 of the B-amyloid Precursor Protein Gene" Nature, vol. 353, pp. 844-846, (1991).

Martin Citron, et al. "Mutation of the B-amyloid Precursor Protein in Familial Alzheimer's Disease Increases B-protein Production" Nature, vol. 360, pp. 672-674, 1992.

George G. Glenner, et al. "Alzheimer's Disease: Initial Report of the Purification and Characterization of a Novel Cerebrovascular Amyloid Protein" Biochem. Biophys. Res. Comm., vol. 120, No. 3, pp. 885-890, 1984.

K. Johnson-Wood, et al. "Amyloid precursor protein processing and AB42 deposition in a transgenic mouse model of Alzheimer disease" Proc.Natl.Acad.Sci.USA, vol. 94, pp. 1550-1555, 1997.

Dennis, J. Selkoe "Amyloid Protein and Alzheimer's Disease" Scientific American, Nov. 1991, pp. 68-78.

Bornemann, K. et al; "Trisubstituted Pyrimidines"; U.S. Appl. No. 10/272,160, filed Oct. 16, 2002.

Dahmann, G. et al; "Pyrimidine Derivatives"; U.S. Appl. No. 10/271,763, filed Oct. 16, 2002.

Dahmann, G. et al; Chemical Abstracts, vol. 138:321292, 2003.

Denny et al., Chemical Abstracts, vol. 134:237498, 2001.

EP Patent Abstracts of Japan; Publication No. 01327790; Patent No. JP 3-127790.

Boschelli, et al; "Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrosine Kinase Inhibitors"; J Med Chem 1998, 41, pp. 4365-4377.

Chemical Abstract: CA 117:48596 for DE 4029650 A1.

Selkoe, D. J., Science, vol. 275 (1997), pp. 630-631.

Selkoe, D. J., Nature, 399 (1999), A23-A31.

Esler, W. P. et al., Nature Cell Biology, 2 (2002), pp. 428-434.

Alzheimer's Disease: Advances in Etiology, Pathogenesis and Therapeutics, Iqbal, K. et al. (ed.), (2001), John Whiley & Sons Ltd., Ch. 72, pp. 777-788.

* cited by examiner

TRISUBSTITUTED PYRIMIDINES

RELATED APPLICATIONS

This application is a continuation of U.S. Non-Provisional Application Ser. No. 10/272,160, filed on Oct. 16, 2002 now abandoned which application claims benefit from U.S. Provisional Application Ser. No. 60/330,128, filed on Oct. 17, 2001.

FIELD OF THE INVENTION

The present invention relates to trisubstituted pyrimidines of formula (I),

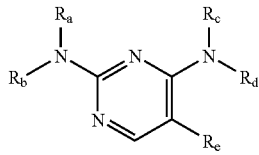

(I)

wherein the groups $R_a$ to $R_e$ have the meanings given in the claims and in the specification, processes for preparing them and the use of compounds of general formula (I) as pharmaceutical compositions, particularly as pharmaceutical compositions for the treatment of illnesses in which the proliferation of cells, particularly endothelial cells, plays a part, or as pharmaceutical compositions with a beta-amyloid-modulating effect.

BACKGROUND OF THE INVENTION

The aggregation and precipitation of proteins are implicated in the origins of various neurodegenerative disorders such as Alzheimer's, Parkinson's and St. Vitus' dance ("Huntington's Chorea"). In Alzheimer's disease the amyloid-β-peptide (Aβ) aggregates and leads to insoluble senile plaques which constitute one of the pathological markers of the disease. Aβ is formed by the proteolytic cleaving of a precursor protein, amyloid precursor protein (APP). Two methods of metabolising APP have been detected, the non-amyloidogenic method and the amyloidogenic method.

In the non-amyloidogenic metabolism of APP, α-secretase cleaves within the Aβ region of the APP and thus leads to the secretion of the soluble N-terminal region of the protein (α-APPs) and, after the γ-secretase cutting has taken place, to the release of p3. By contrast, the amyloidogenic route leads to the formation of Aβ, two proteases generating the N-terminus (β-secretase) and the C-terminus (γ-secretase), respectively, of Aβ.

Aβ can be detected in human plasma and cerebrospinal fluid in vivo. In cell culture, too, secreted Aβ can be detected in the cell culture supernatant of various types of cells which express or overexpress APP or fragments thereof endogenously.

The problem of the present invention is to prepare compounds which are capable of interfering (preferably in an inhibitory capacity) in the process of the formation of Aβ or its release from cells, or of reducing the activity of Aβ by inhibiting it. Finally, the present invention is based on the further objective of preparing compounds which can be used effectively for the prevention or treatment of Alzheimer's disease.

DETAILED DESCRIPTION OF THE INVENTION

The problems set forth above are solved by the compounds of general formula (I) defined as follows.

The compounds according to the invention are trisubstituted pyrimidines of formula (I)

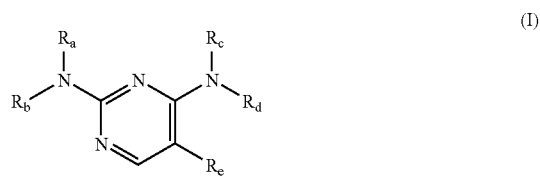

(I)

wherein $R_a$ denotes a hydrogen atom or an alkyl group, $R_b$ denotes a phenyl group substituted by the groups $R_1$ to $R_5$, while $R_1$ denotes a hydrogen, fluorine, chlorine, bromine or iodine atom, a $C_{1-6}$-alkyl, hydroxy or $C_{1-6}$-alkoxy group, a $C_{3-7}$-cycloalkyl, $C_{4-7}$-cycloalkoxy or ($C_{3-7}$-cycloalkyl)alkyl group, which may be substituted in the cycloalkyl moiety by one or two alkyl groups in each case, a $C_{2-5}$-alkenyl, $C_{3-5}$-alkenyloxy, $C_{2-5}$-alkynyl or $C_{3-5}$-alkynyloxy group, wherein the vinyl and ethynyl moieties cannot be linked with an oxygen atom, an aryl, aryloxy, arylalkyl, arylalkoxy, alkylsulphenyl, alkylsulphinyl, alkylsulphonyl, alkylsulphonyloxy, arylsulphenyl, arylsulphinyl, arylsulphonyl, arylalkylsulphenyl, arylalkylsulphinyl or arylalkylsulphonyl group, a methyl, methoxy, methylsulphenyl, methylsulphinyl or methylsulphonyl group substituted by 1 to 3 fluorine atoms, an ethyl, ethoxy, ethylsulphenyl, ethylsulphinyl or ethylsulphonyl group substituted by 1 to 5 fluorine atoms, a nitro, amino, alkylamino, dialkylamino or azido group, an 4- to 7-membered alkyleneimino group optionally substituted by one or two alkyl groups, an 6 or 7-membered alkyleneimino group optionally substituted by one or two alkyl groups, wherein a methylene group in the 4 position to the imino-nitrogen atom is replaced by the group W, where W denotes an oxygen or sulphur atom, a sulphinyl, sulphonyl, imino, N-alkyl-imino, N-formyl-imino, N-alkylcarbonyl-imino, N-cyano-imino, N-alkoxycarbonyl-imino or N-alkylsulphonyl-imino group, a formylamino, N-alkyl-formylamino, alkylcarbonylamino, N-alkyl-alkylcarbonylamino, alkylsulphonylamino or N-alkyl-alkylsulphonylamino group, an alkylcarbonyl, carboxy, alkoxycarbonyl, aminocarbonyl, alkylaminocarbonyl, dialkylaminocarbonyl or cyano group, an aminosulphonyl, alkylaminosulphonyl or dialkylaminosulphonyl group, an alkyl or alkoxy group substituted by $R_9$, wherein $R_9$ denotes a hydroxy, alkoxy, amino, alkylamino, dialkylamino, alkylsulphenyl, alkylsulphinyl, alkylsulphonyl, carboxy, alkoxycarbonyl, aminocarbonyl, alkylaminocarbonyl, dialkylaminocarbonyl or cyano group, a 4- to 7-membered alkyleneiminocarbonyl group optionally substituted by one or two alkyl groups, a 6 or 7-membered alkyleneiminocarbonyl group optionally substituted by one or two alkyl groups, wherein a methylene group in the 4 position of the alkyleneimino moiety is replaced by the group W, where W is as hereinbefore defined, a 4- to 7-membered alkyleneimino group optionally substituted by one or two alkyl groups, a 5- to 7-membered alkyleneimino group optionally substituted by one or two alkyl groups, wherein a methylene group adjacent to the nitrogen atom is replaced by a carbonyl group, a 6- or 7-membered alkyleneimino group optionally substituted by one or two alkyl groups, wherein a methylene group in the 4 position is replaced by the group W, where W is as hereinbefore defined, a formylamino, N-alkyl-formylamino, alkylcarbonylamino, N-alkyl-alkylcarbonylamino, alkylsulphonylamino, N-alkyl-alkylsulphonylamino, perfluoralkylsulphonylamino, N-alkyl-perfluoralkylsulphonylamino, alkoxycarbonylamino, N-alkyl-alkoxycarbonylamino, cyanoamino or N-alkyl-cyanoamino group, $R_2$ and $R_3$ in each case independently of one another denote hydrogen, fluorine, chlorine, bromine or iodine atoms, alkyl, alkoxy, fluoroalkyl, fluoroalkoxy or cyano groups or $R_2$ together with $R_3$, if they are bound to adjacent carbon atoms, also a methylenedioxy group optionally substituted by one or two alkyl groups, an n-$C_{3-6}$-alkylene group optionally substituted by one or two alkyl groups, wherein a methylene group may be replaced by the group W', where W' has the meanings given above for W and additionally denotes a trifluoroacetylimino group, a 1,3-butadiene-1,4-diylene group optionally substituted by a fluorine, chlorine, bromine or iodine atom, by an alkyl, trifluoromethyl, hydroxy, alkoxy, trifluoromethoxy or cyano group, while the abovementioned 1,3-butadiene-1,4-diylene groups may additionally be substituted by a fluorine or chlorine atom, by an alkyl, trifluoromethyl or alkoxy group, $R_4$ and $R_5$ in each case independently of one another denote hydrogen, fluorine or chlorine atoms or $R_4$ together with $R_a$, if $R_4$ is in the o-position to the nitrogen atom substituted by $R_a$, also denote an n-$C_{2-4}$-alkylene group optionally substituted by one or two alkyl groups, $R_c$ denotes a $C_{1-6}$-alkyl group optionally mono- or polysubstituted by $R_9$, while $R_9$ is as hereinbefore defined, a methyl group substituted by a fluoromethyl, chloromethyl, bromomethyl, difluoromethyl or trifluoromethyl group, a $C_{3-7}$-cycloalkyl, ($C_{3-7}$-cycloalkyl)alkyl or arylalkyl group, a $C_{3-5}$-alkenyl or $C_{3-5}$-alkynyl group, wherein the vinyl and ethynyl moieties cannot be linked to the nitrogen atom of the $R_cNR_d$ group, $R_d$ denotes a hydrogen atom or an alkyl group, or $R_c$ together with $R_d$ and the nitrogen atom attached to them denote a 3- to 7-membered alkyleneimino group or a 6 or 7-membered alkyleneimino group, wherein a methylene group in the 4 position is replaced by the group W, where W is as hereinbefore defined, and $R_e$ denotes a nitro, amino, alkylamino, dialkylamino or azido group, a 4- to 7-membered alkyleneimino group optionally substituted by one or two alkyl groups, wherein one or two methylene group adjacent to the nitrogen atoms may be replaced by a carbonyl group, while additionally in this alkyleneimino group a $CH_2$ group in the 4 position may be replaced by the group W where W is as hereinbefore defined, a formylamino, N-alkyl-formylamino, alkylcarbonylamino, N-alkyl-alkylcarbonylamino, di(alkylcarbonyl)amino, ($C_{3-7}$-cycloalkyl)carbonylamino, N-alkyl-($C_{3-7}$-cycloalkyl)carbonylamino, ($C_{3-7}$-cycloalkyl)alkylcarbonylamino, N-alkyl-($C_{3-7}$-cycloalkyl)alkylcarbonylamino, arylcarbonylamino, N-alkyl-arylcarbonylamino, arylalkylcarbonylamino, N-alkyl-arylalkylcarbonylamino, heteroarylcarbonylamino, N-alkyl-heteroarylcarbonylamino, heteroarylalkylcarbonylamino, N-alkyl-heteroarylalkylcarbonylamino, alkoxycarbonylamino, N-alkyl-alkoxycarbonylamino, arylalkoxycarbonylamino, N-alkyl-arylalkoxycarbonylamino, aryloxycarbonylamino, N-alkyl-aryl-oxycarbonylamino, ($C_{4-7}$-cycloalkoxy)carbonylamino, N-alkyl-($C_{4-7}$-cycloalkoxy)carbonylamino, ($C_{3-7}$-cycloalkyl)alkoxycarbonylamino, N-alkyl-($C_{3-7}$-cycloalkyl)alkoxycarbonylamino, alkylsulphonylamino, N-alkyl-alkylsulphonylamino, di(alkylsulphonyl)amino, $C_{3-7}$-cycloalkylsulphonylamino, N-alkyl-$C_{3-7}$-cycloalkylsulphonylamino, ($C_{3-7}$-cycloalkyl)alkylsulphonylamino, N-alkyl-($C_{3-7}$-cycloalkyl)alkylsulphonylamino, arylsulphonylamino, N-alkyl-arylsulphonylamino, arylalkylsulphonylamino, N-alkyl-arylalkylsulphonylamino, heteroarylsulphonylamino, N-alkyl-heteroarylsulphonylamino, heteroarylalkylsulphonylamino, N-alkyl-heteroarylalkylsulphonylamino, cyanoamino or N-alkyl-cyanoamino group, while additionally the alkyl moieties and cycloalkyl moieties in the abovementioned groups may be substituted by the group $R_9$, while $R_9$ is as hereinbefore defined, and the cycloalkyl moieties may additionally be substituted by one or two alkyl groups, a ($C_{5-7}$-cycloalkyl)carbonylamino, N-alkyl-($C_{5-7}$-cycloalkyl)carbonylamino, ($C_{5-7}$-cycloalkyl)alkylcarbonylamino or N-alkyl-($C_{5-7}$-cycloalkyl)alkylcarbonylamino group, while the cycloalkyl moieties may in each case be substituted by one or two alkyl groups and additionally a methylene group in the cycloalkyl moieties of the abovementioned groups is replaced by the group W, where W is as hereinbefore defined, a $C_{2-5}$-alkenylcarbonylamino, N-alkyl-$C_{2-5}$-alkenylcarbonylamino, $C_{2-5}$-alkynylcarbonylamino, N-alkyl-$C_{2-5}$-alkynylcarbonylamino, perfluoroalkylcarbonylamino, N-alkyl-perfluoroalkylcarbonylamino, perchloroalkylcarbonylamino, N-alkyl-perchloroalkylcarbonylamino, perfluoroalkylsulphonylamino or N-alkyl-perfluoroalkylsulphonylamino group, an alkyleneiminocarbonylamino or N-alkyl-alkyleneiminocarbonylamino group optionally substituted in the alkyleneimino moiety by one or two alkyl groups, while the alkyleneimino moiety is 4 to 7-membered in each case, an alkyleneiminocarbonylamino or N-alkyl-alkyleneiminocarbonylamino group optionally substituted in the alkyleneimino moiety by one or two alkyl groups, while the alkyleneimino moiety is 6 or 7-membered in each case and a methylene group in the 4 position of the alkyleneimino moiety is replaced in each case by the group W, where W is as hereinbefore defined, an alkyleneiminothiocarbonylamino or N-alkyl-alkylene-iminothiocarbonylamino group optionally substituted in the alkyleneimino moiety by one or two alkyl groups, while the alkyleneimino moiety is 4 to 7-membered in each case, an alkyleneiminothiocarbonylamino or N-alkyl-alkylene-iminothiocarbonylamino group optionally substituted in the alkyleneimino moiety by one or two alkyl groups, while the alkyleneimino moiety in each case is 6 or 7-membered and a methylene group in the 4 position of the alkyleneimino moiety is replaced in each case by the group W, where W is as hereinbefore defined, a $R_7NR_8$—CO—$NR_6$ or $R_7NR_8$—$SO_2$—$NR_6$-group, wherein $R_6$ denotes a hydrogen atom or an alkyl group, $R_7$ and $R_8$ in each case independently of one another denote hydrogen atoms or alkyl groups optionally substituted by $R_9$, or $R_6$ and $R_7$ together denote an n-$C_{2-3}$-alkylene group and $R_8$ denotes a hydrogen atom or an alkyl group optionally substituted by $R_9$, while $R_9$ is as hereinbefore defined, an imidazolidine-2,4-dion-1-yl or imidazolidine-2,4-dion-3-yl-group optionally substituted by 1 to 3 alkyl groups, while one of the alkyl groups may be substituted by $R_9$, a 1,3-dihydro-imidazol-2-on-1-yl group optionally substituted by 1 to 3 alkyl groups, while one of the alkyl groups may be substituted by $R_9$, a 2,4-dihydro-1,2,4-triazol-3-on-2-yl or 2,4-dihydro-1,2,4-triazol-3-on-4-yl-group optionally substituted by 1 or 2 alkyl groups, while one of the alkyl groups may be substituted by $R_9$, a ($R_{14}NR_{15}$)—$R_{13}C$=N-group wherein $R_{13}$ denotes a hydrogen atom, an alkyl or $C_{3-7}$-cycloalkyl group, $R_{14}$ and $R_{15}$ in each case independently of one another denote an alkyl group, or $R_{14}$ and $R_{15}$ together with the nitrogen atom between them denote a 4- to 7-membered alkyleneimino group optionally substituted by one or two alkyl groups or a 6- or 7-membered alkyleneimino group optionally substituted by one or two alkyl groups, wherein a methylene group in the 4 position is replaced by the group W, where W is as hereinbefore defined, and $R_{13}$ denotes a hydrogen atom, an alkyl or $C_{3-7}$-cycloalkyl group, a ($R_{18}N$=)$CR_{16}$—$R_{17}N$-group wherein $R_{16}$ denotes a hydrogen atom, an alkyl, $C_{3-7}$-cycloalkyl, trifluoromethyl or trichloromethyl group, $R_{17}$ and $R_{18}$, which may be identical or different, in each case represent a hydrogen atom or an alkyl group or $R_{16}$ and $R_{18}$ together represent an n-$C_{3-5}$-alkylene group optionally substituted by one or two alkyl groups and $R_{17}$ represents a hydrogen atom or an alkyl group or $R_{17}$ and $R_{18}$ together represent an n-$C_{2-4}$-alkylene group optionally substituted by one or two alkyl groups and $R_{16}$ denotes a hydrogen atom, an alkyl or $C_{3-7}$-cycloalkyl group, an ($R_{19}R_{20}PO$)—NH-group optionally substituted at the nitrogen atom by an alkyl group, wherein $R_{19}$ and $R_{20}$, which may be identical or different, denote alkyl or aryl groups, a alkyl or alkoxy group substituted by $R_9$, wherein $R_9$ is as hereinbefore defined, a formyl, alkylcarbonyl, 1-(hydroxyimino)alkyl, 1-(alkoxyimino)alkyl, carboxy, alkoxycarbonyl, aminocarbonyl, alkylaminocarbonyl, dialkylaminocarbonyl or cyano group, a sulpho, alkoxysulphonyl, aminosulphonyl, alkylaminosulphonyl or dialkylaminosulphonyl group, a 4- to 7-membered alkyleneiminocarbonyl or alkyleneiminosulphonyl group optionally substituted by one or two alkyl groups, a 6- or 7-membered alkyleneiminocarbonyl or alkyleneiminosulphonyl group optionally substituted by one or two alkyl groups, wherein a methylene group of the alkyleneimino moiety is replaced in the 4 position by the group W, where W is as hereinbefore defined, a heteroaryl or heteroarylalkyl group, an alkoxy-C(=NH) or alkylsulphenyl-C(=NH)-group optionally substituted at the nitrogen atom by an alkyl group, an $R_{10}N$=C($OR_{11}$), $R_{10}N$=C($SR_{11}$), $R_{10}N$=C($NHR_{11}$) or $R_{10}N$=C(N-alkyl-$NR_{11}$)-group, wherein $R_{10}$ and $R_{11}$ together denote an n-$C_{2-4}$-alkylene group optionally substituted by one or two alkyl groups, an amidino group optionally substituted by one to three alkyl groups or an amidino group substituted by a hydroxy, alkoxy, cyano, alkoxycarbonyl or arylalkoxycarbonyl group, which may additionally be substituted at the nitrogen atoms by one or two alkyl groups, the tautomers, the stereoisomers or the physiologically acceptable salts thereof, while, unless otherwise stated, by the aryl moieties mentioned in the definition of the abovementioned groups is meant a phenyl group which may in each case be monosubstituted by $R_{21}$, mono-, di- or trisubstituted by $R_{22}$ or monosubstituted by $R_{21}$ and additionally mono- or disubstituted by $R_{22}$, while the substituents may be identical or different, and $R_{21}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, pyrrolidino, piperidino, morpholino, piperazino or 4-alkyl-piperazino group and $R_{22}$ denotes an alkyl, hydroxy or alkoxy group, a fluorine, chlorine, bromine or iodine atom, while two groups $R_{22}$ if they are bound to adjacent carbon atoms, may also denote an alkylene group with 3 to 6 carbon atoms, a 1,3-butadiene-1,4-diylene group or a methylenedioxy group, while by the heteroaryl moieties is meant a 5-membered heteroaromatic ring with an imino group, an oxygen or sulphur atom or a 5-membered heteroaromatic ring with an oxygen or sulphur atom and one to two nitrogen atoms or a 5-membered heteroaromatic ring with an imino group and one to three nitrogen atoms or a 6-membered heteroaromatic ring with one to three nitrogen atoms, while the abovementioned 5- and 6-membered heteroaromatic rings may be substituted by one to two alkyl groups or by a trifluoromethyl group, and, unless otherwise stated, the abovementioned alkyl, alkylene and alkoxy moieties in each case contain 1 to 4 carbon atoms.

Preferred compounds of general formula (I) are those wherein $R_a$ denotes a hydrogen atom or an alkyl group, $R_b$ denotes a phenyl group substituted by the groups $R_1$ to $R_5$, while $R_1$ denotes a hydrogen, fluorine, chlorine, bromine or iodine atom, a $C_{1-6}$-alkyl, hydroxy or $C_{1-6}$-alkoxy group, a $C_{3-6}$-cycloalkyl, $C_{5-6}$-cycloalkoxy or ($C_{3-6}$-cycloalkyl)alkyl group, which may be substituted in the cycloalkyl moiety by one or two alkyl groups in each case, a $C_{2-5}$-alkenyl, $C_{3-5}$-alkenyloxy, $C_{2-5}$-alkynyl or $C_{3-5}$-alkynyloxy group, wherein the vinyl and ethynyl moieties cannot be linked with an oxygen atom, an aryl, aryloxy, arylalkyl, arylalkoxy, alkylsulphenyl, alkylsulphinyl, alkylsulphonyl, alkylsulphonyloxy, arylsulphenyl, arylsulphinyl, arylsulphonyl, arylalkylsulphenyl, arylalkylsulphinyl or arylalkylsulphonyl group, a methyl, methoxy, methylsulphenyl, methylsulphinyl or methylsulphonyl group substituted by 1 to 3 fluorine atoms, an ethyl, ethoxy, ethylsulphenyl, ethylsulphinyl or ethylsulphonyl group substituted by 1 to 5 fluorine atoms, a nitro, amino, alkylamino, dialkylamino or azido group, a 5- to 6-membered alkyleneimino group optionally substituted by one or two alkyl groups, a 6- or 7-membered alkyleneimino group optionally substituted by one or two alkyl groups, wherein a methylene group in the 4 position to the imino-nitrogen atom is replaced by the group W, where W denotes an oxygen or sulphur atom, a sulphinyl, sulphonyl, imino, N-alkyl-imino, N-formyl-imino, N-alkylcarbonyl-imino, N-cyan-imino, N-alkoxycarbonyl-imino or N-alkylsulphonyl-imino group, a formylamino, N-alkyl-formylamino, alkylcarbonylamino, N-alkyl-alkylcarbonylamino, alkylsulphonylamino or N-alkyl-alkylsulphonylamino group, an alkylcarbonyl, carboxy, alkoxycarbonyl, aminocarbonyl, alkylaminocarbonyl, dialkylaminocarbonyl or cyano group, an aminosulphonyl, alkylaminosulphonyl or dialkylaminosulphonyl group, an alkyl or alkoxy group substituted by $R_9$, wherein $R_9$ denotes a hydroxy, alkoxy, amino, alkylamino, dialkylamino, alkylsulphenyl, alkylsulphinyl, alkylsulphonyl, carboxy, alkoxycarbonyl, aminocarbonyl, alkylaminocarbonyl, dialkylaminocarbonyl or cyano group, a 4- to 7-membered alkyleneimino group optionally substituted by one or two alkyl groups, a 6- or 7-membered alkyleneimino group optionally substituted by one or two alkyl groups, wherein a methylene group in the 4 position is replaced by the group W, where W is as hereinbefore defined, a formylamino, N-alkyl-formylamino, alkylcarbonylamino, N-alkyl-alkylcarbonylamino, alkylsulphonylamino, N-alkyl-alkylsulphonylamino, perfluoroalkylsulphonylamino, N-alkyl-perfluoroalkylsulphonylamino, alkoxycarbonylamino, N-alkyl-alkoxycarbonylamino, cyanoamino or N-alkyl-cyanoamino group, $R_2$ and $R_3$ in each case independently of one another denote hydrogen, fluorine, chlorine, bromine or iodine atoms, alkyl, alkoxy, trifluoromethyl, trifluoromethoxy, difluoromethyl, difluoromethoxy or cyano groups or $R_2$ together with $R_3$, if they are bound to adjacent carbon atoms, also denote a methylenedioxy group optionally substituted by one or two alkyl groups, an n-$C_{3-6}$-alkylene group optionally substituted by one or two alkyl groups, wherein a methylene group may be replaced by the group W', where W' has the meanings given above for W and additionally denotes a trifluoroacetylimino group, a 1,3-butadiene-1,4-diylene group optionally substituted by a fluorine, chlorine, bromine or iodine atom, by an alkyl, trifluoromethyl, hydroxy, alkoxy, trifluoromethoxy or cyano group, while the abovementioned 1,3-butadiene-1,4-diylene groups may additionally be substituted by a fluorine or chlorine atom, by an alkyl, trifluoromethyl or alkoxy group, $R_4$ and $R_5$, which may be identical or different, denote hydrogen, fluorine or chlorine atoms, $R_c$ denotes a $C_{1-6}$-alkyl group, which may be substituted by one or more hydroxy, alkoxy, dialkylamino groups, $R_d$ denotes a hydrogen atom or a $C_{1-6}$-alkyl group, and $R_e$ denotes a nitro, amino, alkylamino, dialkylamino or azido group, a 5- to 7-membered alkyleneimino group optionally substituted by one or two alkyl groups, a 5- to 7-membered alkyleneimino group optionally substituted by one or two alkyl groups, wherein one or two methylene groups adjacent to the nitrogen atoms may be replaced by a carbonyl group, while additionally in the alkyleneimino group a methylene group in the 4 position to the imino-nitrogen atom may be replaced by the group W where W is as hereinbefore defined, a formylamino, N-alkyl-formylamino, alkylcarbonylamino, N-alkyl-alkylcarbonylamino, di(alkylcarbonyl)amino, ($C_{3-7}$-cycloalkyl)carbonylamino, N-alkyl-($C_{3-7}$-cycloalkyl)carbonylamino, ($C_{3-7}$-cycloalkyl)alkylcarbonylamino, N-alkyl-($C_{3-7}$-cycloalkyl)alkylcarbonylamino, arylcarbonylamino, N-alkyl-arylcarbonylamino, arylalkylcarbonylamino, N-alkyl-arylalkylcarbonylamino, heteroarylcarbonylamino, N-alkyl-heteroarylcarbonylamino, heteroarylalkylcarbonylamino, N-alkyl-heteroarylalkylcarbonylamino, alkoxycarbonylamino, N-alkyl-alkoxycarbonylamino, arylalkoxycarbonylamino, N-alkyl-arylalkoxycarbonylamino, aryloxycarbonylamino, N-alkyl-aryl-oxycarbonylamino, ($C_{4-7}$-cycloalkoxy)carbonylamino, N-alkyl-($C_{4-7}$-cycloalkoxy)carbonylamino, ($C_{3-7}$-cycloalkyl)alkoxycarbonylamino, N-alkyl-($C_{3-7}$-cycloalkyl)alkoxycarbonylamino, alkylsulphonylamino, N-alkyl-alkylsulphonylamino, di(alkylsulphonyl)amino, $C_{3-7}$-cycloalkylsulphonylamino, N-alkyl-$C_{3-7}$-cycloalkylsulphonylamino, ($C_{3-7}$-cycloalkyl)alkylsulphonylamino, N-alkyl-($C_{3-7}$-cycloalkyl)alkylsulphonylamino, arylsulphonylamino, N-alkyl-arylsulphonylamino, arylalkylsulphonylamino, N-alkyl-arylalkylsulphonylamino, heteroarylsulphonylamino, N-alkyl-heteroarylsulphonylamino, heteroarylalkylsulphonylamino, N-alkyl-heteroarylalkylsulphonylamino, cyanoamino or N-alkyl-cyanoamino group, while in each case the alkyl moiety of these groups may be substituted by the group $R_9$ and $R_9$ is as hereinbefore defined, and the cycloalkyl moieties of these groups may be substituted by one or two alkyl groups and additionally a $CH_2$ group in the cycloalkyl moieties of the abovementioned groups is replaced by the group W, where W is as hereinbefore defined, a $C_{2-5}$-alkenylcarbonylamino, N-alkyl-$C_{2-5}$-alkenylcarbonylamino, $C_{2-5}$-alkynylcarbonylamino, N-alkyl-$C_{2-5}$-alkynylcarbonylamino, perfluoroalkylcarbonylamino, N-alkyl-perfluoroalkylcarbonylamino, perchloroalkylcarbonylamino, N-alkyl-perchloroalkylcarbonylamino, perfluoroalkylsulphonylamino or N-alkyl-perfluoroalkylsulphonylamino group, an alkyleneiminocarbonylamino or N-alkyl-alkyleneiminocarbonylamino group optionally substituted in the alkyleneimino moiety by one or two alkyl groups, while the alkyleneimino moiety is 4- to 7-membered in each case, an alkyleneiminocarbonylamino or N-alkyl-alkyleneiminocarbonylamino group optionally substituted in the alkyleneimino moiety by one or two alkyl groups, while the alkyleneimino moiety is 6- or 7-membered in each case and a methylene group in the 4 position of the alkyleneimino moiety is in each case replaced by the group W, where W is as hereinbefore defined, an alkyleneiminothiocarbonylamino or N-alkyl-alkyleneiminothiocarbonylamino group optionally substituted in the alkyleneimino moiety by one or two alkyl groups, while the alkyleneimino moiety is 4- to 7-membered in each case, an alkyleneiminothiocarbonylamino or N-alkyl-alkyleneiminothiocarbonylamino group optionally substituted in the alkyleneimino moiety by one or two alkyl groups, while the alkyleneimino moiety is 6- or 7-membered in each case and in each case a methylene group in the 4 position of the alkyleneimino moiety is replaced by the group W, where W is as hereinbefore defined, a $R_7NR_8$—CX—$NR_6$ or $R_7NR_8$—$SO_2$—$NR_6$-group, wherein $R_6$ denotes a hydrogen atom or an alkyl group, $R_7$ and $R_8$, which may be identical or different, denote hydrogen atoms or alkyl groups optionally substituted by $R_9$ or $R_6$ and $R_7$ together denote an n-$C_{2-3}$-alkylene group and $R_8$ denotes a hydrogen atom or an alkyl group optionally substituted by $R_9$, while $R_9$ is as hereinbefore defined, and X denotes O or S, an imidazolidine-2,4-dion-1-yl or imidazolidine-2,4-dion-3-yl-group optionally substituted by an alkyl group, a $(R_{14}NR_{15})$—$R_{13}C$=N-group wherein $R_{13}$ denotes a hydrogen atom, an alkyl or $C_{3-7}$-cycloalkyl group, $R_{14}$ and $R_{15}$, which may be identical or different, in each case denote an alkyl group, or $R_{14}$ and $R_{15}$ together with the nitrogen atom between them denote a 4- to 7-membered alkyleneimino group optionally substituted by one or two alkyl groups or a 6- or 7-membered alkyleneimino group optionally substituted by one or two alkyl groups, wherein a methylene group in the 4 position is replaced by the group W, where W is as hereinbefore defined, and $R_{13}$ denotes a hydrogen atom, an alkyl or $C_{3-7}$-cycloalkyl group, a $(R_{18}N=)CR_{16}$—$R_{17}N$-group, wherein $R_{16}$ denotes a hydrogen atom, an alkyl, $C_{3-7}$-cycloalkyl, trifluoromethyl or trichloromethyl group, $R_{17}$ and $R_{18}$ in each case independently of one another denote a hydrogen atom or an alkyl group, or $R_{16}$ and $R_{18}$ together denote an n-$C_{3-5}$-alkylene group optionally substituted by one or two alkyl groups, and $R_{17}$ denotes a hydrogen atom or an alkyl group, or $R_{17}$ and $R_{18}$ together denote an n-$C_{2-4}$-alkylene group optionally substituted by one or two alkyl groups, and $R_{16}$ denotes a hydrogen atom, an alkyl or $C_{3-7}$-cycloalkyl group, an $(R_{19}R_{20}PO)$—NH-group optionally substituted at the nitrogen atom by an alkyl group wherein $R_{19}$ and $R_{20}$, which may be identical or different, denote alkyl groups, an alkyl or alkoxy group substituted by $R_9$, wherein $R_9$ is as hereinbefore defined, a formyl, alkylcarbonyl, 1-(hydroxyimino)alkyl, 1-(alkoxyimino)alkyl, carboxy, alkoxycarbonyl, aminocarbonyl, alkylaminocarbonyl, dialkylaminocarbonyl or cyano group, a sulpho, alkoxysulphonyl, aminosulphonyl, alkylaminosulphonyl or dialkylaminosulphonyl group, a 4- to 7-membered alkyleneiminocarbonyl or alkyleneiminosulphonyl group optionally substituted by one or two alkyl groups, a 6 or 7-membered alkyleneiminocarbonyl or alkyleneiminosulphonyl group optionally substituted by one or two alkyl groups, wherein a methylene group of the alkyleneimino moiety in the 4 position is replaced by the group W, where W is as hereinbefore defined, a heteroaryl or heteroarylalkyl group, an alkoxy-C(=NH) or alkylsulphenyl-C(=NH)-group optionally substituted at the nitrogen atom by an alkyl group, an $R_{10}N$=$C(OR_{11})$, $R_{10}N$=$C(SR_{11})$, $R_{10}N$=$C(NHR_{11})$ or $R_{10}N$=$C(N$-alkyl-$NR_{11})$-group, wherein $R_{10}$ and $R_{11}$ together denote an n-$C_{2-4}$-alkylene group optionally substituted by one or two alkyl groups, an amidino group optionally substituted by one to three alkyl groups or an amidino group substituted by a hydroxy, alkoxy, cyano, alkoxycarbonyl or arylalkoxycarbonyl group, which may additionally be substituted at the nitrogen atoms by one or two alkyl groups, by the aryl moieties mentioned in the definition of the abovementioned groups is meant a phenyl group which may in each case be monosubstituted by $R_{21}$, mono-, di- or trisubstituted by $R_{22}$ or monosubstituted by $R_{21}$ and additionally mono- or disubstituted by $R_{22}$, while the substituents may be identical or different, and $R_{21}$ denotes a cyano, carboxy, aminocarbonyl, alkylaminocarbonyl, dialkylaminocarbonyl, alkoxycarbonyl, alkylcarbonyl, alkylsulphenyl, alkylsulphinyl, alkylsulphonyl, alkylsulphonyloxy, perfluoroalkyl, perfluoroalkoxy, nitro, amino, alkylamino, dialkylamino, alkylcarbonylamino, phenylalkylcarbonylamino, phenylcarbonylamino, alkylsulphonylamino, phenylalkylsulphonylamino, phenylsulphonylamino, N-alkyl-alkylcarbonylamino, N-alkyl-phenylalkylcarbonylamino, N-alkyl-phenylcarbonylamino, N-alkyl-alkylsulphonylamino, N-alkyl-phenylalkylsulphonylamino, N-alkyl-phenylsulphonylamino, aminosulphonyl, alkylaminosulphonyl, dialkylaminosulphonyl, pyrrolidino, piperidino, morpholino, piperazino or 4-alkyl-piperazino group and $R_{22}$ denotes an alkyl, hydroxy or alkoxy group, a fluorine, chlorine, bromine or iodine atom, while two groups $R_{22}$, if they are bound to adjacent carbon atoms, may also denote an alkylene group with 3 to 6 carbon atoms, a 1,3-butadiene-1,4-diylene group or a methylenedioxy group, while by the heteroaryl moieties is meant a 5-membered heteroaromatic ring with an imino group, an oxygen or sulphur atom or a 5-membered heteroaromatic ring with an oxygen or sulphur atom and one to two nitrogen atoms or a 5-membered heteroaromatic ring with an imino group and one to three nitrogen atoms or a 6-membered heteroaromatic ring with one to three nitrogen atoms, while the abovementioned 5- and 6-membered heteroaromatic rings may be substituted by one to two alkyl groups or by a trifluoromethyl group, and, unless otherwise stated, the abovementioned alkyl, alkylene and alkoxy moieties in each case contain 1 to 4 carbon atoms.

the tautomers, the stereoisomers and the salts thereof.

Particularly preferred compounds of general formula (I) are those wherein $R_a$ denotes a hydrogen atom or a methyl group, $R_b$ denotes a phenyl group substituted by the groups $R_1$ to $R_5$, while $R_1$ denotes a hydrogen, fluorine, chlorine, bromine or iodine atom,
an alkyl, hydroxy or alkoxy group,
a $C_{3-6}$-cycloalkyl or $C_{5-6}$-cycloalkoxy group,
a $C_{2-4}$-alkenyl, $C_{3-4}$-alkenyloxy, $C_{2-4}$-alkynyl or $C_{3-4}$-alkynyloxy group,
wherein the vinyl and ethynyl moieties cannot be linked with an oxygen atom,
a phenyl, phenyloxy, phenylalkyl, phenylalkoxy, alkylsulphenyl, alkylsulphinyl,
alkylsulphonyl or alkylsulphonyloxy group,
a methyl or methoxy group substituted by 1 to 3 fluorine atoms,
an ethyl or ethoxy group substituted by 1 to 5 fluorine atoms,
a nitro, amino, alkylamino, dialkylamino or azido group,
a pyrrolidino, piperidino, morpholino, piperazino or 4-methyl-piperazino group,
an alkylcarbonylamino, N-alkyl-alkylcarbonylamino, alkylsulphonylamino or N-alkyl-alkylsulphonylamino group,
an alkylcarbonyl, carboxy, alkoxycarbonyl, aminocarbonyl, alkylaminocarbonyl, dialkylaminocarbonyl or cyano group,
an aminosulphonyl, alkylaminosulphonyl or dialkylaminosulphonyl group, an alkyl or alkoxy group substituted by $R_9$, where
$R_9$ denotes a hydroxy, $C_{1-2}$-alkoxy, amino, $C_{1-2}$-alkylamino, di-($C_{1-2}$-alkyl)-amino, carboxy, $C_{1-2}$-alkoxycarbonyl, aminocarbonyl, $C_{1-2}$-alkylaminocarbonyl, di-($C_{1-2}$-alkyl)-aminocarbonyl or cyano group,
a 4- to 6-membered alkyleneimino group, a morpholino, piperazino or 4-methyl-piperazino group,
an alkylcarbonylamino, N-methyl-alkylcarbonylamino, alkylsulphonylamino, N-methyl-alkylsulphonylamino, alkoxycarbonylamino or N-methyl-alkoxycarbonylamino group, $R_2$ denotes a hydrogen, fluorine, chlorine or bromine atom, a methyl, methoxy, trifluoromethyl or cyano group, $R_3$ denotes a hydrogen, fluorine or chlorine atom, or $R_2$ together with $R_3$, if they are bound to adjacent carbon atoms, also denote a methylenedioxy group, an n-$C_{3-5}$-alkylene group, wherein a methylene group may be replaced by an imino, N-methyl-imino or N-trifluoroacetyl-imino group, or a 1,3-butadiene-1,4-diylene group optionally substituted by a fluorine or chlorine atom, by a methyl, methoxy or trifluoromethyl group, $R_4$ and $R_5$, which may be identical or different, denote hydrogen or fluorine atoms, $R_c$ denotes a methyl, ethyl or propyl group which may be substituted by a hydroxy, alkoxy, dialkylamino group, $R_d$ denotes a hydrogen atom or a methyl group, and $R_e$ denotes a nitro, amino, alkylamino or dialkylamino group, a pyrrolidino, piperidino, morpholino, piperazino, 4-methyl-piperazino, 2-oxo-pyrrolidino, 2-oxo-piperidino, 2,5-dioxo-pyrrolidino or 2,6-dioxo-piperidino group,
a formylamino, N-alkyl-formylamino, alkylcarbonylamino, N-alkyl-alkylcarbonylamino, $C_{3-6}$-cycloalkylcarbonylamino, N-alkyl-$C_{3-6}$-cycloalkylcarbonylamino, ($C_{3-6}$-cycloalkyl)alkylcarbonylamino, N-alkyl-($C_{3-6}$-cycloalkyl)alkylcarbonylamino, phenylcarbonylamino, N-alkyl-phenylcarbonylamino, phenylalkylcarbonylamino, N-alkyl-phenylalkylcarbonylamino, alkoxycarbonylamino, N-alkyl-alkoxycarbonylamino, phenylalkoxycarbonylamino, N-alkyl-phenylalkoxycarbonylamino, phenyloxycarbonylamino, N-alkyl-phenyloxycarbonylamino, alkylsulphonylamino, N-alkyl-alkylsulphonylamino, di(methylsulphonyl)amino, $C_{3-6}$-cycloalkylsulphonylamino, N-alkyl-$C_{3-6}$-cycloalkylsulphonylamino, ($C_{3-6}$-cycloalkyl)alkylsulphonylamino, N-alkyl-($C_{3-6}$-cycloalkyl)alkylsulphonylamino, phenylsulphonylamino, N-alkyl-phenylsulphonylamino, phenylalkylsulphonylamino, N-alkyl-phenylalkylsulphonylamino, cyanoamino, N-alkyl-cyanoamino, trifluoroacetylamino, N-alkyl-trifluoroacetylamino, trifluoromethylsulphonylamino or N-alkyl-trifluoromethylsulphonylamino group, an alkylcarbonylamino or N-alkyl-alkylcarbonylamino group, while in each case the alkyl moiety of the alkylcarbonyl group is substituted by the group $R_9$, where $R_9$ is as hereinbefore defined,
a pyrrolidinocarbonylamino, piperidinocarbonylamino, homopiperidinocarbonylamino, morpholinocarbonylamino, homomorpholinocarbonylamino, piperazinocarbonylamino, 4-alkylcarbonylpiperazinocarbonylamino, 4-alkylsulphonylpiperazinocarbonylamino or 4-alkylpiperazinocarbonylamino group which in each case may be substituted at the carbonylamino moiety by an alkyl group,
a pyrrolidinothiocarbonylamino, piperidinothiocarbonylamino, morpholinothiocarbonylamino, piperazinothiocarbonylamino or 4-alkylpiperazinothiocarbonylamino group which may be substituted in each case at the thiocarbonylamino moiety by an alkyl group,
a $R_7NR_8$—CO—$NR_6$ or $R_7NR_8$—$SO_2$—$NR_6$ group, wherein $R_6$ denotes a hydrogen atom or an alkyl group, $R_7$ and $R_8$ in each case independently of one another denote hydrogen atoms or alkyl groups optionally substituted by $R_9$, or $R_6$ and $R_7$ together denote an n-$C_{2-3}$-alkyl group, and $R_8$ denotes a hydrogen atom or an alkyl group optionally substituted by $R_9$, while $R_9$ is as hereinbefore defined,
an imidazolidine-2,4-dion-1-yl or imidazolidine-2,4-dion-3-yl-group optionally substituted by an alkyl group, a ($R_{14}NR_{15}$)—$R_{13}C$=N-group wherein
$R_{13}$ denotes a hydrogen atom or an alkyl group,
$R_{14}$ and $R_{15}$ in each case independently of one another denote an alkyl group or
$R_{14}$ and $R_{15}$ together with the nitrogen atom between them denote a pyrrolidino, piperidino, morpholino, piperazino or 4-alkyl-piperazino group,
a ($R_{18}N$=)$CR_{16}$–$R_{17}$N-group wherein
$R_{16}$ denotes an alkyl or trichloromethyl group,
$R_{17}$ denotes a hydrogen atom or an alkyl group and
$R_{18}$ denotes a hydrogen atom, a dialkylphosphinylamino group optionally substituted at the nitrogen atom by an alkyl group, wherein the alkyl substituents may be identical or different, a carboxy, alkoxycarbonyl, aminocarbonyl, alkylaminocarbonyl, dialkylaminocarbonyl or cyano group, an aminosulphonyl, alkylaminosulphonyl or dialkylaminosulphonyl group, a pyrrolidinocarbonyl, piperidinocarbonyl, morpholinocarbonyl, piperazinocarbonyl, 4-alkyl-piperazinocarbonyl, pyrrolidinosulphonyl, piperidinosulphonyl, morpholinosulphonyl, piperazinosulphonyl or 4-alkyl-piperazinosulphonyl group, an optionally by a methyl group substituted pyrrolyl, furyl, thienyl, imidazolyl, 1,2,4-triazolyl, tetrazolyl, oxazolyl, thiazolyl, pyridyl, pyrimidyl, 1,3,4-oxadiazolyl or 1,3,4-thiadiazolyl group,
an $R_{10}N$=$C(OR_{11})$, $R_{10}N$=$C(NHR_{11})$ or $R_{10}N$=$C(N$-alkyl-$NR_{11}$)-group, wherein
$R_{10}$ and $R_{11}$ together denote an n-$C_{2-3}$-alkylene group optionally substituted by one or two methyl groups,
an amidino group optionally substituted by one to three alkyl groups or an amidino group substituted by a hydroxy, alkoxy, cyano, alkoxycarbonyl or phenylalkoxycarbonyl group, which may additionally be substituted at the nitrogen atoms by one or two methyl groups, while, unless otherwise stated, the phenyl groups mentioned in the definition of the abovementioned groups may be substituted in each case by a fluorine, chlorine or bromine atom or by a methyl, methoxy or trifluoromethyl group, and, unless otherwise stated, the abovementioned alkyl, alkylene and alkoxy moieties each contain 1 to 4 carbon atoms, the tautomers, the stereoisomers and the salts thereof Of particular importance according to the invention are compounds of general formula (I) wherein
$R_a$ denotes a hydrogen atom or a methyl group,
$R_b$ denotes a phenyl group substituted by the groups $R_1$ to $R_5$, while
$R_1$ denotes a hydrogen, fluorine, chlorine, bromine or iodine atom,
a $C_{1-4}$-alkyl, hydroxy or $C_{1-4}$-alkoxy group,
an ethynyl, phenyl, phenyloxy or benzyloxy group,
a methylsulphenyl, methylsulphinyl or methylsulphonyl group,
a trifluoromethyl, trifluoromethoxy or 1,1,2,2-tetrafluoroethoxy group,
a nitro, dimethylamino or azido group,
a morpholino group,
an acetylamino or methylsulphonylamino group,
an acetyl, carboxy, $C_{1-2}$-alkoxycarbonyl, aminocarbonyl or cyano group,
an aminosulphonyl group,
a $C_{1-2}$-alkyl group which is substituted by a methoxy, amino, $C_{1-2}$-alkylamino, di-($C_{1-2}$-alkyl)-amino, carboxy, $C_{1-2}$-alkoxycarbonyl, pyrrolidino, piperidino, morpholino, piperazino, 4-methyl-piperazino, acetylamino, methyl-sulphonylamino or $C_{1-4}$-alkoxycarbonylamino group,
an ethoxy group which is substituted in the 2 position by an amino, or $C_{1-4}$-alkoxycarbonylamino group,
$R_2$ denotes a hydrogen, fluorine or chlorine atom or a methyl group,
$R_3$ denotes a hydrogen, fluorine or chlorine atom or
$R_2$ together with $R_3$, if they are bound to adjacent carbon atoms, also denote an n-$C_{3-4}$-alkylene group, an —$CH_2CH_2NHCH_2CH_2$-group optionally substituted at the nitrogen atom by a methyl or trifluoroacetyl group, or a 1,3-butadiene-1,4-diylene group,
$R_4$ and $R_5$ in each case independently of one another denote hydrogen or fluorine atoms,
$R_c$ denotes a methyl, ethyl or propyl group, which may be terminally substituted by a hydroxy, methoxy or dimethylamino group,
$R_d$ denotes a hydrogen atom or a methyl group,
$R_e$ denotes a nitro or amino group,
a formylamino, $C_{1-4}$-alkylcarbonylamino, cyclopropylcarbonylamino, phenylcarbonylamino, $C_{1-3}$-alkoxycarbonylamino, benzyloxycarbonylamino, phenyloxycarbonylamino, $C_{1-4}$-alkylsulphonylamino, N-methyl-methylsulphonylamino, di(methylsulphonyl)amino, phenylsulphonylamino, benzylsulphonylamino, trifluoroacetylamino, dimethylaminosulphonylamino, dimethylphosphinylamino, 1-iminoethylamino, 1-imino-2,2,2-trichloroethylamino or N',N'-dimethyl-N-formamidino group,
a pyrrolidinocarbonylamino, piperidinocarbonylamino, homopiperidinocarbonylamino, morpholinocarbonylamino, piperazinocarbonylamino, 4-methylpiperazinocarbonylamino or 4-acetylpiperazinocarbonylamino group which may be substituted by a methyl group at the carbonylamino moiety in each case,
a morpholinothiocarbonylamino group,
a $R_7NR_8$—CO—$NR_6$-group wherein
$R_6$ denotes a hydrogen atom or a methyl group, and
$R_7$ and $R_8$ in each case independently of one another represent hydrogen atoms or $C_{1-3}$-alkyl groups, while the alkyl groups may be terminally substituted by a hydroxy, methoxy, dimethylamino or $C_{1-2}$-alkoxycarbonyl group, or
$R_6$ and $R_7$ together denote a n-$C_{2-3}$-alkylene group, and
$R_8$ denotes a hydrogen atom or a methyl group,
an imidazolidine-2,4-dion-3-yl-group,
a carboxy, $C_{1-2}$-alkoxycarbonyl or cyano group,
an aminosulphonyl, methylaminosulphonyl or dimethylaminosulphonyl group,
a 1-pyrrolyl or 5-tetrazolyl group, the tautomers, the stereoisomers and the salts thereof.

Also preferred are compounds of general formula (I), wherein
$R_a$ and $R_d$ each independently of one another represent a hydrogen atom or a methyl group,
$R_b$ denotes a phenyl group substituted by one or two fluorine or chlorine atoms,
$R_c$ a methyl, ethyl or propyl group, which may be terminally substituted by a dimethylamino group, the tautomers, the stereoisomers and the salts thereof.

Of exceptional importance according to the invention are the compounds of general formula (I), wherein
$R_e$ denotes a nitro, acetylamino, trifluoroacetylamino, methylsulphonamino or amino group, or a urea group of formula

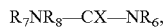

wherein $R_6$ denotes a hydrogen atom or an alkyl group, $R_7$ and $R_8$, which may be identical or different, denotes hydrogen atoms or alkyl groups optionally substituted by hydroxy, methoxy or dimethylamino, or $R_6$ and $R_7$ together denote an n-$C_{2-3}$-alkylene group, and $R_8$ denotes a hydrogen atom or an alkyl group optionally substituted by hydroxy, methoxy or dimethylamino, or $R_7$ and $R_8$ taken together denote a $C_{4-8}$-alkylenediyl group, while one or two non-adjacent $CH_2$ groups may be replaced by —O—, —S— or —$NR_{23}$—, wherein $R_{23}$ denotes a hydrogen atom, a $C_{1-3}$-alkyl group or $C_{1-3}$-alkanoyl group, and X denotes O or S, the tautomers, the stereoisomers and the salts thereof.

The following compounds are mentioned as being particularly important within the scope of the present invention:

2-(4-chloroanilino)-4-methylamino-5-nitro-pyrimidine
2-(3,4-dichloroanilino)-4-methylamino-5-amino-pyrimidine
2-(3,4-dichloroamino)-4-methylamino-5-methylsulphonamino-pyrimidine
2-(3,4-dichloroanilino)-4-(3-dimethylaminopropyl)-amino-5-nitro-pyrimidine
2-(3,4-dichloroanilino)-4-methylamino-5-acetamido-pyrimidine
2-(3,4-dichloroanilino)-4-methylamino-5-(N-methyl-N-methylsulphonylamino)-pyrimidine
2-(3,4-dichloroanilino)-4-methylamino-5-(2-oxo-imidazolidin-1-yl)-pyrimidine
2-(3,4-dichloroanilino)-4-methylamino-5-(morpholin-1-ylcarbonylamino)-pyrimidine
2-(3,4-dichloroanilino)-4-methylamino-5-($N^2,N^2$-dimethylureido)-pyrimidine
2-[N-(3,4-dichlorophenyl)-N-methylamino]-4-methylamino-5-(2-oxo-imidazolidin-1-yl)-pyrimidine
2-(3,4-dichloroanilino)-4-methylamino-5-(2-oxo-tetrahydropyrimidin-1-yl)-pyrimidine
2-(3,4-dichloroanilino)-4-methylamino-5-ureido-pyrimidine
2-(3,4-dichloroanilino)-4-dimethylamino-5-(morpholin-1-ylcarbonylamino)-pyrimidine
2-(3,4-dichloroanilino)-4-ethylamino-5-(morpholin-1-ylcarbonylamino)-pyrimidine
2-(3-chloroanilino)-4-methylamino-5-(morpholin-1-ylcarbonylamino)-pyrimidine
2-(3,4-dichloroanilino)-4-methylamino-5-(pyrrolidin-1-ylcarbonylamino)-pyrimidine
2-(3,4-dichloroanilino)-4-methylamino-5-(4-methylpiperazin-1-ylcarbonylamino)-pyrimidine
2-(3,4-dichloroanilino)-4-methylamino-5-[$N^2,N^2$-di-(2-methoxyethyl)-ureido]-pyrimidine
2-(3,4-dichloroanilino)-4-methylamino-5-(azepanyl-1-carbonylamino)-pyrimidine
2-(3,4-dichloroanilino)-4-methylamino-5-($N^2,N^2$-diethylureido)-pyrimidine
2-(3,4-dichloroanilino)-4-methylamino-5-(piperazin-1-ylcarbonylamino)-pyrimidine
2-(3,4-dichloroanilino)-4-methylamino-5-(4-acetylpiperazin-1-ylcarbonylamino)-pyrimidine
2-(3,4-dichloroanilino)-4-methylamino-5-[$N^2$-methyl-$N^2$-(2-hydroxyethyl)-ureido]-pyrimidine
2-(3,4-dichloroanilino)-4-methylamino-5-(morpholin-1-ylthiocarbonylamino)-pyrimidine
2-(3,4-dichloroanilino)-4-methylamino-5-(2,2,2-trifluoroacetamido)-pyrimidine
2-(3,4-dichloroanilino)-4-methylamino-5-[$N^2$-methyl-$N^2$-(2-dimethylaminoethyl)-ureido]-pyrimidine 2-(3,4-dichloroamino)-4-methylamino-5-[$N^2$-methyl-$N^2$-(3-dimethylaminopropyl)-ureido]-pyrimidine and the salts thereof.

The invention relates to the compounds in question, optionally in the form of the individual optical isomers, mixtures of the individual enantiomers or racemates, in the form of the tautomers and in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The term alkyl groups (including those which are part of other groups) denotes branched and unbranched alkyl groups with 1 to 4 carbon atoms, unless otherwise specified. Examples include: methyl, ethyl, propyl and butyl. Unless otherwise stated, the above terms propyl and butyl also include all the possible isomeric forms. Accordingly, the term propyl also includes the two isomeric groups n-propyl and iso-propyl and the term butyl includes n-butyl, iso-butyl, sec. butyl and tert.-butyl. In some cases common abbreviations are also used to denote the abovementioned alkyl groups, such as Me for methyl, Et for ethyl etc.

The term alkylene groups denotes branched and unbranched alkylene bridges with 1 to 4 carbon atoms. Examples include: methylene, ethylene, propylene and butylene. Unless otherwise stated, the terms propylene and butylene used above also include all the possible isomeric forms. Accordingly, the term propylene also includes the two isomeric bridges n-propylene and dimethylmethylene and the term butylene includes the isomeric bridges n-butylene, 1-methylpropylene, 2-methylpropylene, 1,1-dimethylethylene and 1,2-dimethylethylene.

The term alkenyl groups (including those which are part of other groups) denotes branched and unbranched alkenyl groups with 2 to 4 carbon atoms, provided that they have at least one double bond, such as, for example, vinyl (provided that no unstable enamines or enolethers are formed), propenyl, iso-propenyl and butenyl.

The term halogen generally denotes fluorine, chlorine, bromine or iodine. Unless otherwise specified, chlorine is preferred within the scope of the present invention.

"=O" denotes an oxygen atom linked via a double bond.

In another aspect, the present invention relates to the use of the compounds of formula (I) defined above as pharmaceutical compositions. In particular, the present invention relates to the use of the compounds of formula (I) for preparing a pharmaceutical composition for the prevention and/or treatment of diseases in which a therapeutic benefit can be achieved by interfering (preferably in an inhibitory capacity) in the process of the formation of Aβ or its release from cells. It is preferred according to the invention to use compounds of general formula (I) as specified above in order to prepare a pharmaceutical composition for the prevention and/or treatment of Alzheimer's disease.

The present invention thus further relates to pharmaceutical compositions containing at least one compound of the above formula I, the tautomers, the stereoisomers or the physiologically acceptable salts thereof, the use thereof for the treatment of diseases in which the proliferation of cells, particularly endothelial cells, is involved, and processes for the preparation thereof.

One approach to synthesising the compounds of general formula (I) according to the invention may involve the use of various methods, optionally based on or using conventional chemical methods of synthesis as described in more detail hereinafter.

As a rule, the compounds of formula (I) are prepared by:
a. reacting a compound of formula

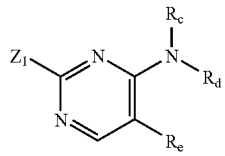

(II)

wherein
$R_c$ to $R_e$ are defined as in claims 1 to 8 and
$Z_1$ denotes a leaving group, with an amine of formula H—($R_a$N$R_b$)   (III)

wherein
$R_a$ and $R_b$ are defined as in claims 1 to 8.

The reaction is expediently carried out in a solvent such as ethanol, isopropanol, butanol, tetrahydrofuran, dioxane, toluene, chlorobenzene, dimethylformamide, dimethylsulphoxide, ethyleneglycolmonomethylether, ethyleneglycoldiethylether or sulpholane, optionally in the presence of an inorganic base, e.g. sodium carbonate or potassium hydroxide, or a tertiary organic base, e.g. triethylamine, N-ethyl-diisopropylamine or pyridine, while the latter may simultaneously serve as solvent, and optionally in the presence of a reaction accelerator such as a copper salt, a corresponding amine-hydrohalide or alkali metal halide at temperatures between 0 and 250° C., preferably however at temperatures between 20 and 200° C. The reaction may, however, also be carried out without a solvent or in an excess of the compound of general formula III used.

b. reacting a compound of formula IV

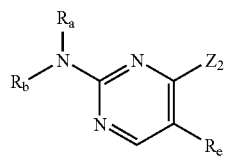

(IV)

wherein
$R_a$, $R_b$ and $R_e$, are defined as in claims 1 to 8, and
$Z_2$ denotes a leaving group, with an amine of formula H—($R_c$N$R_d$)   (V)

wherein
$R_c$ and $R_d$ are defined as in claims 1 to 8.

The reaction is expediently carried out in a solvent such as ethanol, isopropanol, butanol, tetrahydrofuran, dioxane, toluene, chlorobenzene, dimethylformamide, dimethylsulphoxide, ethyleneglycolmonomethylether, ethyleneglycoldiethylether or sulpholane, optionally in the presence of an inorganic base, e.g. sodium carbonate or potassium hydroxide, or a tertiary organic base, e.g. triethylamine, N-ethyl-diisopropylamine or pyridine, while the latter may simultaneously serve as solvent, and optionally in the presence of a reaction accelerator such as a copper salt, a corresponding amine-hydrohalide or alkali metal halide at temperatures between 0 and 250° C., preferably however at temperatures between 20 and 200° C. The reaction may however also be carried out without a solvent or in an excess of the compound of general formula V used.

c. in order to prepare a compound of formula I wherein $R_e$ denotes an amino group, reducing a compound of formula I wherein $R_e$ denotes a nitro group and optionally converting a compound of formula I thus obtained according to the invention with a free amino or imino group, by reacting with an electrophil selected from among the isocyanates, isothiocyanates, carboxylic acids, sulphonic acids or their reactive derivatives, into a corresponding compound of formula I.

The reduction is conveniently carried out hydrogenolytically, e.g. with hydrogen in the presence of a catalyst such as platinum, palladium/charcoal or Raney nickel in a suitable solvent such as methanol, ethanol, ethyl acetate, tetrahydrofuran, dioxane, dimethylformamide or glacial acetic acid, optionally with the addition of an acid such as hydrochloric acid and at a hydrogen pressure of 1 to 7 bar, preferably however 1 to 5 bar, with metals such as iron, tin or zinc in the presence of an acid such as acetic acid or hydrochloric acid, with salts such as iron(II)sulphate, tin (II)chloride, sodium sulphide, sodium hydrogen sulphite or sodium dithionite, or with hydrazine in the presence of Raney nickel at temperatures between 0 and 100° C., preferably however between 20 and 60° C.

A compound of formula I thus obtained which contains an amino, alkylamino or imino group is converted by alkylation or reductive alkylation into a corresponding alkyl compound of formula I; and/or a compound of formula I thus obtained which contains an amino, alkylamino or imino group is converted by amidation with a corresponding acetimino derivative into a corresponding amidino compound of formula I; and/or a compound of formula I thus obtained which contains a carboxy group is converted by esterification into a corresponding ester of formula I and/or a compound of formula I thus obtained which contains a carboxy or ester group is converted by amidation into a corresponding amide of formula I and/or if necessary any protecting group used during the reactions to protect reactive groups is cleaved; and/or if desired a compound of formula I thus obtained is then resolved into the stereoisomers thereof; and/or a compound of formula I thus obtained is converted into the salts thereof, particularly for pharmaceutical use into the physiologically acceptable salts thereof with an inorganic or organic acid or base.

The subsequent acylation or sulphonylation is conveniently carried out with a corresponding halide, anhydride or isocyanate in a solvent such as methylene chloride, chloroform, carbon tetrachloride, ether, tetrahydrofuran, dioxane, benzene, toluene, acetonitrile or sulpholane, optionally in the presence of an inorganic or organic base at temperatures between −20 and 200° C., preferably however at temperatures between −10 and 160° C. However, it may also be carried out with the free acid, optionally in the presence of an acid-activating agent or a dehydrating agent, e.g. in the presence of isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole, N,N'-carbonyldiimidazole or N,N'-thionyldiimidazole or triphenylphosphine/carbon tetrachloride, at temperatures between −20 and 200° C., preferably however at temperatures between −10 and 160° C.

The subsequent esterification is optionally carried out in a solvent or mixture of solvents such as methylene chloride, dimethylformamide, benzene, toluene, chlorobenzene, tetrahydrofuran, benzene/tetrahydrofuran or dioxane or, particularly advantageously, in a corresponding alcohol, optionally in the presence of an acid such as hydrochloric acid or in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenyl-phosphine/carbon tetrachloride, conveniently at temperatures between 0 and 150° C., preferably at temperatures between 0 and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran, dioxane, dimethylsulphoxide or sulpholane with an alkylating agent such as a corresponding halide or sulphonic acid ester, e.g. with methyl iodide, ethyl bromide, dimethylsulphate or benzyl chloride, optionally in the presence of a tertiary organic base or in the presence of an inorganic base conveniently at temperatures between 0 and 150° C., preferably at temperatures between 0 and 100° C.

The subsequent reductive alkylation is carried out with a corresponding carbonyl compound such as formaldehyde, acetaldehyde, propionaldehyde, acetone or butyraldehyde in the presence of a complex metal hydride such as sodium borohydride, lithium borohydride or sodium cyanoborohydride, conveniently at a pH value of 6–7 and at ambient temperature or in the presence of a hydrogenation catalyst, e.g. with hydrogen in the presence of palladium/charcoal, at a hydrogen pressure of 1 to 5 bar. The methylation is however preferably carried out in the presence of formic acid as reducing agent at elevated temperatures, e.g. at temperatures between 60 and 120° C.

The subsequent amidation is carried out by reacting a corresponding reactive carboxylic acid derivative with a corresponding amine, optionally in a solvent or mixture of solvents such as methylene chloride, dimethylformamide, benzene, toluene, chlorobenzene, tetrahydrofuran, glacial acetic acid, benzene/tetrahydrofuran or dioxane, while the amine used may simultaneously act as solvent, optionally in the presence of a tertiary organic base or in the presence of an inorganic base or with a corresponding carboxylic acid in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, O-(benzotriazol-1-yl)-N,N,N',N'-tetramethyluronium-tetrafluoroborate, N,N'-dicyclohexylcarbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, conveniently at temperatures between 0 and 150° C., preferably at temperatures between 0 and 80° C.

The subsequent oxidation is preferably carried out in a solvent or mixture of solvents, e.g. in water, water/pyridine, acetone, methylene chloride, acetic acid, acetic acid/acetic anhydride, dilute sulphuric acid or trifluoroacetic acid, conveniently at temperatures between −80 and 100° C. depending on the oxidising agent used.

In order to prepare a corresponding sulphinyl compound of general formula I the oxidation is conveniently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid, optionally in the presence of a weak base such as sodium acetate, with N-bromosuccinimide in ethanol, with tert.butyl hypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphurylchloride in methylene chloride at −70° C., the resulting thioether-chlorine complex is conveniently hydrolysed with aqueous ethanol.

In order to prepare a sulphonyl compound of general formula I the oxidation is conveniently carried out, starting from a corresponding sulphinyl compound, with one or more equivalents of the oxidising agent used or, starting from a corresponding sulphenyl compound, conveniently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

A mixture of a corresponding sulphinyl and sulphonyl compound of general formula I optionally obtained in this way may subsequently, if desired, be separated by known methods, e.g. by chromatography.

The subsequent preparation of a compound of general formula I which contains a tetrazole group is preferably carried out in a solvent such as benzene, toluene or dimethylformamide at temperatures between 80 and 150° C., preferably at 120 and 130° C. The hydrohalic acid required is conveniently librated during the reaction from an alkali metal azide, e.g. from sodium azide, in the presence of a weak acid such as ammonium chloride. The reaction may also be carried out with a different salt or derivative of hydrohalic acid, preferably with aluminium azide or tributyl tin azide, in which case the tetrazole compound optionally obtained in this way is liberated from the salt contained in the reaction mixture by acidification with a dilute acid such as 2N hydrochloric acid or 2N sulphuric acid.

The subsequent conversion of a compound of general formula I which contains a hydroxyalkyl group into a corresponding haloalkyl compound is preferably carried out with a halogen-introducing agent such as phosphorus oxychloride or thionyl chloride in a solvent such as methylene chloride at temperatures between 0 and the boiling temperature of the reaction mixture.

The subsequent conversion of a compound of formula I which contains a haloalkyl group into a corresponding aminoalkyl compound of general formula I is preferably carried out in a solvent such as methylene chloride or acetonitrile or in an excess of the amine used as solvent and optionally in the presence of a tertiary organic base at temperatures between 0 and 150° C., preferably at temperatures between 20 and 80° C.

The subsequent conversion of a compound of general formula I which contains a hydroxyethylaminocarbonylamino group into a corresponding imidazolidinone of general formula I is preferably carried out in a solvent such as tetrahydrofuran in the presence of a dehydrating agent such as triphenylphosphine/ethyl azodicarboxylate at temperatures between 0 and 50° C., preferably at temperatures between 0 and 150° C.

The subsequent conversion of a compound of general formula I which contains an amino group into a corresponding 1-pyrrolo compound of general formula I is preferably carried out in a solvent such as glacial acetic acid with 2,5-dimethoxy-tetrahydrofuran at temperatures between 20 and 150° C., preferably at temperatures between 100 and 150° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, a protecting group for a carboxyl group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides may be, for example, a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to V used as starting materials are known from the literature in some cases or may be obtained by methods known from the literature.

As already mentioned earlier, the compounds of formula I according to the invention and the physiologically acceptable salts thereof have valuable pharmacological properties, particularly the property of inhibiting the process of the formation of Aβ in cells or its release from cells. This property was investigated according to the test described below.

The inhibition of Aβ formation was investigated using the following test system:

Preparation of a suitable γ-secretase HTS cell line:

H4 neuroglioma cells (Accession number HTB 148 at the "American Type Culture Collection", Manassas, Va., USA) were transfected under standard conditions with the reporter construct pFRLuc (Stratagene) which carries the gene for luciferase. By transient transfection experiments with pcDNA3-Gal4 which codes for the soluble Gal4, an individual clone having the highest luciferase activity was selected. In order to prepare the Aβ-KKK/Gal4 construct, a sequence containing the N-terminal signal sequence of APP and the first 55 amino acids of Aβ (Shoji et al, 1992) was linked to the Gal4 coding sequence (Laughan, A and Gesteland, R Molec. Cell Biol., 1984, 4: 260–267) by genetic engineering and cloned into the expression vector pcDNA3neo (Invitrogen). This construct was called pcDNA3-AβKKK/Gal4. In order to insert an ER-retention signal in the substrate of the γ-secretase, the last nucleotides of the Gal4 were altered by genetic engineering so that they coded for the amino acids KKLI. This construct was named Aβ-KKK-ER. The cell clone obtained as described above was used for the second stable transfection with pcDNA3-Aβ-KKK/Gal4 or pcDNA3-Aβ-KKK-ER and the selection with neomycin was carried out under standard conditions (Sambrook and Maniatis, 1989). Individual neomycin-resistant cell clones were investigated for their expression of luciferase. The clones with the highest expression were used for the substance analyses. All the transfections were carried out using the Fugene transfection system supplied by Boehringer Mannheim, in accordance with the manufacturer's instructions.

HTS Assay Principle

The doubly stabile HTS cell line is seeded onto a 96/384 microtitre plate. When the cells are confluent, they are incubated with the particular test substance for a specified length of time. After incubation the cell medium is removed and the luciferase enzyme activity is determined precisely as instructed by the manufacturer of the test kit used (Steady-Glo, Promega).

As a result of the presence of an endogenous γ-secretase activity in the H4 cells the substrate (Aβ-KKK/Gal4) is cleaved proteolytically, while the transactivator Gal4 is able to become detached from the membrane and enter the cell nucleus. In the cell nucleus Gal4 binds to the Gal4-DNA binding domain of the reporter construct and thus activates the expression of the luciferase. If a specific γ-secretase inhibitor is present the substrate cannot be cleaved and Gal4 remains bound to the substrate on the cell membrane, leading to a reduction amounting to total inhibition of the luciferase activity.

Cells are seeded on 96/384 well plates in DMEM complete medium (10% FCS, 1% glutamine, 1% penicillin/ streptomycin) in a dilution of 1:5. The cells are incubated for 24 to 48 h (depending on the cell clone and the dilution used) at 37° C., 5% $CO_2$ and allowed to grow until 80–90% confluence is achieved. Then the test substance is added and the preparation is incubated overnight (8–16 h) at 37° C. and 5% $CO_2$. The 96/384 well plates are equilibrated to ambient temperature (RT). The "Steady-Glo" Luciferase Assay System Kit (Promega catalogue no. E2520) is used. The Luciferase Assay Reagent is thawed and equilibrated to ambient temperature or freshly prepared (Luciferase Assay Substrate dissolved in Luciferase Assay Buffer). The medium is suction filtered to remove the cells. 100 μl (based on 96 well plates) of fresh complete medium are added per well. 100 μl (based on 96 well plates) of Luciferase Assay Reagent are added and the preparation is incubated for 5 min at RT. Then the luminescence is measured. For 384 well plates the quantities pipetted are reduced accordingly.

The measurements are compared with the control and then the IC50 is determined from a number of measurements.

The IC50 values obtained for the compounds according to the invention are shown in Table 1.

TABLE 1

| Example | IC50 [nM] |
|---|---|
| 1 (1) | 800 |
| 2 (1) | 1000 |
| 3 (3) | 60 |
| 3 (4) | 60 |
| 3 (26) | 600 |
| 3 (30) | 200 |
| 3 (33) | 300 |
| 3 (36) | 250 |
| 3 (40) | 350 |
| 3 (54) | 900 |
| 3 (55) | 900 |
| 3 (59) | 150 |
| 3 (66) | 800 |
| 4 (9) | 1000 |
| 8 | 1100 |
| 8 (2) | 1000 |
| 11 | 100 |
| 11 (2) | 100 |
| 11 (3) | 4 |
| 11 (4) | 60 |
| 11 (5) | 100 |
| 11 (6) | 700 |
| 11 (7) | 1000 |
| 11 (8) | 200 |
| 11 (10) | 800 |
| 11 (11) | 700 |
| 11 (12) | 1000 |

The examples of synthesis that follow serve only as an illustration without restricting the object of the invention thereto.

EXAMPLE I 2-(4-Chlorophenylamino)-4-thiocyanato-5-nitro-pyrimidine 19.7 g of 4-chloroaniline in 70 ml of ethanol are added within 15 minutes to 15.9 g of 2-chloro-4-thiocyanato-5-nitro-pyrimidine in 210 ml toluene at a maximum temperature of 10° C. The mixture is stirred for another 30 minutes at 10° C., the solid is removed by suction filtering, washed with ethanol and dried.

Yield: 19.0 g (84% of theory), melting point: 224–226° C.

The following compound is obtained analogously to Example I:

(1) 2-(3,4-dichlorophenylamino)-4-thiocyanato-5-nitro-pyrimidine, melting point: 240–242° C.

EXAMPLE II 2-chloro-4-methylamino-5-methoxycarbonyl-pyrimidine 19.1 g of potassium carbonate in 50 ml water are added dropwise to 13 g of 2,4-dichloro-5-methoxycarbonyl-pyrimidine and 4.7 g of methylamine-hydrochloride in 500 ml acetone at 0 to 5° C. within one hour. Then the mixture is stirred for one hour in an ice bath. The acetone is largely removed in vacuo and the residue is distributed between water and ethyl acetate. Then the aqueous phase is extracted twice more with ethyl acetate. The combined organic phases are dried and evaporated down. The residue is separated by chromatography through a silica gel column with cyclohexane/ethyl acetate (2:1).

Yield: 8.8 g (69% of theory), melting point: 121° C.

The following compounds are obtained analogously to Example II:

(1) 2-chloro-4-methylamino-5-trifluoromethyl-pyrimidine, melting point: 123° C.
(2) 2-chloro-4-methylamino-5-cyano-pyrimidine, melting point: 161° C.
(3) 2-chloro-4-methylamino-5-methylaminosulphonyl-pyrimidine Prepared from 2,4-dichloro-5-chlorosulphonyl-pyrimidine and methylamine in methylene chloride at −15° C., $R_f$ value: 0.43 (silica gel; methylene chloride/methanol=20:1)

(4) 2-chloro-4-methylamino-5-methylsulphenyl-pyrimidine, melting point: 130° C.
(5) 2-chloro-4-methylamino-5-(4-methoxybenzylsulphenyl)-pyrimidine, $R_f$ value: 0.62 (silica gel; cyclohexane/ethyl acetate=2:1)
(6) 2-methylsulphenyl-4-methylamino-5-nitro-6-dimethylamino-pyrimidine Starting material: 2-methylsulphenyl-4-methylamino-5-nitro-6-chloro-pyrimidine, melting point: 128–132° C.

(7) 2-methylsulphenyl-4,6-bis(methylamino)-5-nitro-pyrimidine, melting point: 193–196° C.
(8) 2-methylsulphenyl-4-methylamino-5-nitro-6-amino-pyrimidine, melting point: 279–281° C.
(9) 2-methylsulphenyl-4-methylamino-5-nitro-6-methoxy-pyrimidine, melting point: 140° C.

EXAMPLE III 3-(tert.butyloxycarbonylaminomethyl)-4-chloro-aniline a) 2-aminomethyl-4-chloro-nitrobenzene Prepared from 3-cyano-4-chloro-nitrobenzene by reacting with borane-dimethylsulphide in tetrahydrofuran.

$R_f$ value: 0.18 (silica gel; petroleum ether/ethyl acetate=1:1)

b) 3-(tert.butyloxycarbonylaminomethyl)-4-chloro-nitrobenzene

Prepared from 3-cyano-4-chloro-nitrobenzene by reacting with di-tert.butyl pyrrocarbonate in dioxane/sodium hydroxide solution, melting point: 77° C.

c) 3-(tert.butyloxycarbonylaminomethyl)-4-chloro-aniline

Prepared from 3-(tert.butyloxycarbonylaminomethyl)-4-chloro-nitrobenzene by hydrogenation in methanol at ambient temperature in the presence of platinum on charcoal, melting point: 75–77° C.

EXAMPLE IV 4-(tert.butyloxycarbonylaminomethyl)-aniline

Prepared from 4-(tert.butyloxycarbonylaminomethyl)-nitrobenzene by hydrogenation in methanol at ambient temperature in the presence of palladium/charcoal (10% palladium).

$R_f$ value: 0.50 (silica gel; cyclohexane/ethyl acetate=1:1)

EXAMPLE V

3-[2-(tert.butyloxycarbonylamino)ethoxy]-aniline a) 3-[2-(tert.butyloxycarbonylamino)ethoxy]-nitrobenzene Prepared from 3-(2-aminoethoxy)-nitrobenzene-hydrochloride by reacting with di-tert.butyl pyrrocarbonate in dioxane in the presence of aqueous sodium hydroxide solution, $R_f$ value: 0.70 (silica gel; petroleum ether/ethyl acetate=1:1)

b) 3-[2-(tert.butyloxycarbonylamino)ethoxy]-aniline

Prepared from 3-[2-(tert.butyloxycarbonylamino)ethoxy]-nitrobenzene by hydrogenation in methanol at ambient temperature in the presence of platinum/charcoal, $R_f$ value: 0.42 (silica gel; petroleum ether/ethyl acetate=1:1)

EXAMPLE VI

4-[2-(tert.butyloxycarbonylamino)ethoxy]-aniline a) 4-[2-(tert.butyloxycarbonylamino)ethoxy]-nitrobenzene Prepared analogously to the compound of Example Va), $R_f$ value: 0.18 (Reversed Phase silica gel; methanol/5% saline solution=6:4)

b) 4-[2-(tert.butyloxycarbonylamino)ethoxy]-aniline

Prepared analogously to the compound of Example Vb), $R_f$ value: 0.13 (silica gel; cyclohexane/ethyl acetate=1:1)

EXAMPLE VII 2-methylsulphinyl-4-methylamino-5-phenyl-pyrimidine and 2-methylsulphonyl-4-methylamino-5-phenyl-pyrimidine a) 2-methylsulphenyl-4-chloro-5-phenyl-pyrimidine Prepared from 2-methylsulphenyl-4-hydroxy-5-phenyl-pyrimidine by reacting with phosphorus oxychloride at reflux temperature, melting point: 99° C.

b) 2-methylsulphenyl-4-methylamino-5-phenyl-pyrimidine

Prepared from 2-methylsulphenyl-4-chloro-5-phenyl-pyrimidine by reacting with methylamine in ethanol at 90° C., $R_f$ value: 0.63 (silica gel; methylene chloride/methanol=20:1)

c) 2-methylsulphinyl-4-methylamino-5-phenyl-pyrimidine and 2-methylsulphonyl-4-methylamino-5-phenyl-pyrimidine Prepared from 2-methylsulphenyl-4-methylamino-5-phenyl-pyrimidine by reacting with 3-chloro-peroxybenzoic acid in methylene chloride, $R_f$ value: 0.33 and 0.43 (silica gel; methylene chloride/methanol=20:1)

EXAMPLE VIII 2-methylsulphonyl-4-methylamino-5-chloro-pyrimidine a) 2-methylsulphenyl-4-methylamino-5-chloro-pyrimidine Prepared from 2-methylsulphenyl-4,5-dichloro-pyrimidine by reacting with methylamine in ethanol at 90° C., melting point: 241° C., $R_f$ value: 0.59 (silica gel; cyclohexane/ethyl acetate=2:1)

b) 2-methylsulphonyl-4-methylamino-5-chloro-pyrimidine

Prepared from 2-methylsulphenyl-4-methylamino-5-chloro-pyrimidine by reacting with sodium periodate in glacial acetic acid/water, $R_f$ value: 0.50 (silica gel; methylene chloride/methanol=9:1)

EXAMPLE IX 2-methylsulphinyl-4-methylamino-5-methoxy-pyrimidine and 2-methylsulphonyl-4-methylamino-5-methoxy-pyrimidine a) 2-methylsulphenyl-4-methylamino-5-methoxy-pyrimidine Prepared from 2-methylsulphenyl-4-chloro-5-methoxy-pyrimidine by reacting with methylamine in ethanol at 90° C., $R_f$ value: 0.22 (silica gel; cyclohexane/ethyl acetate=2:1)

b) 2-methylsulphinyl-4-methylamino-5-methoxy-pyrimidine and 2-methylsulphonyl-4-methylamino-5-methoxy-pyrimidine Prepared from 2-methylsulphenyl-4-methylamino-5-methoxy-pyrimidine by reacting with sodium periodate in glacial acetic acid/water, $R_f$ value: 0.24 and 0.39 (silica gel; methylene chloride/methanol/conc. aqueous ammonia=20:1:0.1)

EXAMPLE X 2-methylsulphinyl-4-methylamino-5-methyl-pyrimidine a) 2-methylsulphenyl-4-methylamino-5-methyl-pyrimidine Prepared from 2-methylsulphenyl-4-chloro-5-methyl-pyrimidine by reacting with methylamine in ethanol at 100° C., melting point: 134° C., $R_f$ value: 0.35 (silica gel; methylene chloride/methanol=40:1)

b) 2-methylsulphinyl-4-methylamino-5-methyl-pyrimidine

Prepared from 2-methylsulphenyl-4-methylamino-5-methyl-pyrimidine by reacting with 3-chloro-peroxybenzoic acid in methylene chloride, $R_f$ value: 0.23 (silica gel; methylene chloride/methanol/ conc. aqueous ammonia=20:1:0.1)

EXAMPLE XI 2-methylsulphinyl-4-methylamino-5-fluoro-pyrimidine and 2-methylsulphonyl-4-methylamino-5-fluoro-pyrimidine a) 2-methylsulphenyl-4-methylamino-5-fluoro-pyrimidine Prepared from 2-methylsulphenyl-4-chloro-5-fluoro-pyrimidine by reacting with methylamine in ethanol at 100° C., $R_f$ value: 0.53 (silica gel; methylene chloride/methanol/ conc. aqueous ammonia=20:1:0.1)

b) 2-methylsulphinyl-4-methylamino-5-fluoro-pyrimidine and 2-methylsulphonyl-4-methylamino-5-fluoro-pyrimidine Prepared from 2-methylsulphenyl-4-methylamino-5-fluoro-pyrimidine by reacting with 3-chloro-peroxybenzoic acid in methylene chloride, $R_f$ value: 0.27 and 0.42 (silica gel; methylene chloride/methanol=20:1)

EXAMPLE XII 2,4-dichloro-5-(4-methoxybenzylsulphenyl)-pyrimidine a) 2-methylsulphenyl-4-hydroxy-5-(4-methoxybenzylsulphenyl)-pyrimidine Prepared from methyl 4-methoxybenzylsulphenyl-acetate and ethyl formate in the presence of sodium and subsequent reaction with S-methylisothiourea-sulphate in ethanol, $R_f$ value: 0.4 (silica gel; methylene chloride/methanol/conc. aqueous ammonia=20:1:0.1)

b) 2,4-dihydroxy-5-(4-methoxybenzylsulphenyl)-pyrimidine

Prepared from 2-methylsulphenyl-4-hydroxy-5-(4-methoxybenzylsulphenyl)-pyrimidine by treating with hydrochloric acid, melting point: 277° C.

c) 2,4-dichloro-5-(4-methoxybenzylsulphenyl)-pyrimidine

Prepared from 2,4-dihydroxy-5-(4-methoxybenzylsulphenyl)-pyrimidine by treating with phosphorus oxychloride in the presence of N,N-diethylaniline, $R_f$ value: 0.78 (silica gel; cyclohexane/ethyl acetate=2:1)

EXAMPLE XIII 2-methylsulphinyl-4,6-bis-(methylamino)-5-nitro-pyrimidine

Prepared from 2-methylsulphenyl-4,6-bis(methylamino)-5-nitro-pyrimidine by reacting with m-chloroperbenzoic acid, $R_f$ value: 0.36 (silica gel; methylene chloride/methanol=3:1)

EXAMPLE XIV 2-methylsulphinyl-4-methylamino-5-nitro-6-amino-pyrimidine

Prepared from 2-methylsulphenyl-4-methylamino-5-nitro-6-amino-pyrimidine by reacting with m-chloro-perbenzoic acid, melting point: 229–234° C.

EXAMPLE XV 2-methyl sulphinyl-4-methylamino-5-nitro-6-dimethylamino-pyrimidine Prepared from 2-methylsulphenyl-4-methylamino-5-nitro-6-dimethylamino-pyrimidine by reacting with m-chloroperbenzoic acid, $R_f$ value: 0.33 (silica gel; methylene chloride/methanol=95:5)

EXAMPLE XVI 2-methylsulphonyl-4-methylamino-5-nitro-6-methoxy-pyrimidine

Prepared from 2-methylsulphenyl-4-methylamino-5-nitro-6-methoxy-pyrimidine by reacting with sodium periodate in acetic acid, $R_f$ value: 0.24 (silica gel; methylene chloride)

EXAMPLE 1

2-(3,4-dichlorophenylamino)-4-methylamino-5-nitro-pyrimidine 6.47 g of 2-chloro-4-methylamino-5-nitro-pyrimidine and 11.7 g of 3,4-dichloro-aniline are heated to 160° C. in 60 ml of sulpholane within 45 minutes in an oil bath. After 40 minutes stirring at this temperature the reaction mixture is cooled and added to 600 ml of ice water. The precipitate is suction filtered, washed repeatedly with water and dried. The residue is stirred for one hour with 100 ml of ethyl acetate, the precipitate is suction filtered, washed with ethyl acetate and dried.

Yield: 9.8 g (90% of theory), melting point: 271–273° C.

The following compounds are obtained analogously to Example 1:

(1) 2-(4-chlorophenylamino)-4-methylamino-5-nitro-pyrimidine, melting point: 235–237° C.
(2) 2-phenylamino-4-methylamino-5-nitro-pyrimidine, melting point: 266° C.
(3) 2-(4-chloro-3-fluoro-phenylamino)-4-methylamino-5-nitro-pyrimidine, melting point: 246° C.
(4) 2-[N-(4-chlorophenyl)-methylamino]-4-methylamino-5-nitro-pyrimidine, melting point: 180° C.
(5) 2-(4-chloro-2-fluoro-phenylamino)-4-methylamino-5-nitro-pyrimidine, melting point: 232° C.
(6) 2-(2-trifluoromethylphenylamino)-4-methylamino-5-nitro-pyrimidine, melting point: 134° C.
(7) 2-(3,4,5-trichlorophenylamino)-4-methylamino-5-nitro-pyrimidine, melting point: 307° C.
(8) 2-(3-chloro-4-fluorophenylamino)-4-methylamino-5-nitro-pyrimidine, melting point: 243° C.
(9) 2-(N-methyl-phenylamino)-4-methylamino-5-nitro-pyrimidine, melting point: 128° C.
(11) 2-(2-methylphenylamino)-4-methylamino-5-nitro-pyrimidine, melting point: 242° C.
(12) 2-(3-methylphenylamino)-4-methylamino-5-nitro-pyrimidine, melting point: 254° C.
(15) 2-(4-methylphenylamino)-4-methylamino-5-nitro-pyrimidine, melting point: 238° C.
(16) 2-(2-methoxyphenylamino)-4-methylamino-5-nitro-pyrimidine, melting point: 247° C.
(17) 2-(3-methoxyphenylamino)-4-methylamino-5-nitro-pyrimidine, melting point: 174° C.
(18) 2-(4-methoxyphenylamino)-4-methylamino-5-nitro-pyrimidine, melting point: 239° C.
(19) 2-(4-bromophenylamino)-4-methylamino-5-nitro-pyrimidine, melting point: 235° C.
(20) 2-(4-fluorophenylamino)-4-methylamino-5-nitro-pyrimidine, melting point: 210° C.
(21) 2-(2-chlorophenylamino)-4-methylamino-5-nitro-pyrimidine, melting point: 190° C.
(22) 2-(3-cyanophenylamino)-4-methylamino-5-nitro-pyrimidine, melting point: 250–255° C.
(23) 2-[4-(dimethylamino)phenylamino]-4-methylamino-5-nitro-pyrimidine, melting point: 253° C.
(24) 2-(3-trifluoromethylphenylamino)-4-methylamino-5-nitro-pyrimidine, melting point: 179° C.
(25) 2-(3-chlorophenylamino)-4-methylamino-5-nitro-pyrimidine, melting point: 244° C.
(26) 2-(4-trifluoromethylphenylamino)-4-methylamino-5-nitro-pyrimidine, melting point: 257° C.
(27) 2-(4-iodophenylamino)-4-methylamino-5-nitro-pyrimidine, melting point: 259° C.
(28) 2-(3,4-difluorophenylamino)-4-methylamino-5-nitro-pyrimidine, melting point: 256° C.
(29) 2-(3,4-dimethylphenylamino)-4-methylamino-5-nitro-pyrimidine, melting point: 245° C.
(30) 2-(4-chloro-3-trifluoromethylphenylamino)-4-methylamino-5-nitro-pyrimidine, melting point: 239° C.
(31) 2-(4-chloro-3-methylphenylamino)-4-methylamino-5-nitro-pyrimidine, melting point: 247° C.
(32) 2-(4-chloro-3-cyanophenylamino)-4-methylamino-5-nitro-pyrimidine, melting point: 280–283° C.
(33) 2-(3-bromo-4-chlorophenylamino)-4-methylamino-5-nitro-pyrimidine, melting point: 265° C.
(34) 2-[3-(tert.butyloxycarbonylaminomethyl)-4-chlorophenylamino]-4-methylamino-5-nitro-pyrimidine
Carried out in the presence of N-ethyl-diisopropylamine, melting point: 195° C.
(36) 2-(4-chlorophenylamino)-4-dimethylamino-5-nitro-pyrimidine, melting point: 198° C.
(40) 2-(3,4-dichlorophenylamino)-4-dimethylamino-5-nitro-pyrimidine, melting point: 208° C.

(41) 2-(3,4-dichlorophenylamino)-4-methylamino-5-nitro-6-methyl-pyrimidine, melting point: 220–222° C.

(43) 2-(3-trifluoroacetyl-2,3,4,5-tetrahydro-1H-3-benzazepin-7-yl-amino)-4-methylamino-5-nitro-pyrimidine, melting point: 242–243° C.

(45) 2-[4-(tert.butyloxycarbonylaminomethyl)-phenylamino]-4-methylamino-5-nitro-pyrimidine Carried out in the presence of N-ethyl-diisopropylamine, melting point: 260° C.

(47) 2-[4-[2-(tert.butyloxycarbonylamino)ethyl]-phenylamino]-4-methylamino-5-nitro-pyrimidine Carried out in the presence of N-ethyl-diisopropylamine, $R_f$ value: 0.52 (silica gel; cyclohexane/ethyl acetate=1:1)

(48) 2-[3-(aminomethyl)-phenylamino]-4-methylamino-5-nitro-pyrimidine-dihydrochloride, melting point: >350° C., $R_f$ value: 0.58 (Reversed Phase silica gel; acetonitrile/water=1:1 with 1% trifluoroacetic acid)

(49) 2-(4-azidophenylamino)-4-methylamino-5-nitro-pyrimidine

Carried out in the presence of N-ethyl-diisopropylamine, $R_f$ value: 0.42 (silica gel; petroleum ether/ethyl acetate=4:1), Mass spectrum: $M^+$=286

(53) 2-[3-[2-(tert.butyloxycarbonylamino)ethoxy]phenylamino]-4-methylamino-5-nitro-pyrimidine Carried out in the presence of N-ethyl-diisopropylamine, melting point: 193° C.

(54) 2-(4-chlorophenylamino)-4-methylamino-5-nitro-6-methyl-pyrimidine, melting point: 196–201° C.

(55) 2-[4-[2-(tert.butyloxycarbonylamino)ethyl]-phenylamino]-4-methylamino-5-nitro-pyrimidine Carried out in the presence of N-ethyl-diisopropylamine, melting point: 70–71° C.

(57) 2-(4-ethylphenylamino)-4-methylamino-5-nitro-pyrimidine, melting point: 228° C.

(58) 2-(4-isopropylphenylamino)-4-methylamino-5-nitro-pyrimidine, melting point: 236° C.

(59) 2-(4-phenoxyphenylamino)-4-methylamino-5-nitro-pyrimidine, melting point: 227° C.

(60) 2-(5-indanylamino)-4-methylamino-5-nitro-pyrimidine, melting point: 233° C.

(61) 2-(4-butoxyphenylamino)-4-methylamino-5-nitro-pyrimidine, melting point: 211° C.

(62) 2-(4-tert.butylphenylamino)-4-methylamino-5-nitro-pyrimidine, melting point: 229° C.

(63) 2-(4-ethoxyphenylamino)-4-methylamino-5-nitro-pyrimidine, melting point: 220° C.

(64) 2-(4-morpholinophenylamino)-4-methylamino-5-nitro-pyrimidine, melting point: 253° C.

(65) 2-(4-benzyloxyphenylamino)-4-methylamino-5-nitro-pyrimidine, melting point: 246° C.

(66) 2-(4-acetylamino-phenylamino)-4-methylamino-5-nitro-pyrimidine, melting point: 289° C.

(67) 2-(3-nitrophenylamino)-4-methylamino-5-nitro-pyrimidine, melting point: 269° C.

(68) 2-(4-biphenylylamino)-4-methylamino-5-nitro-pyrimidine, melting point: 300–302° C.

(69) 2-(4-methylsulphenyl-phenylamino)-4-methylamino-5-nitro-pyrimidine, melting point: 250° C.

(70) 2-(2-naphthylamino)-4-methylamino-5-nitro-pyrimidine, melting point: 286° C.

(71) 2-(4-acetylphenylamino)-4-methylamino-5-nitro-pyrimidine, melting point: 295° C.

(72) 2-(4-aminosulphonyl-phenylamino)-4-methylamino-5-nitro-pyrimidine, melting point: 323° C.

(73) 2-(3-aminocarbonyl-phenylamino)-4-methylamino-5-nitro-pyrimidine, melting point: 317° C.

(74) 2-[3-(1,1,2,2-tetrafluoroethoxy)phenylamino]-4-methylamino-5-nitro-pyrimidine, melting point: 218° C.

(75) 2-[4-(2-methoxycarbonylethyl)phenylamino]-4-methylamino-5-nitro-pyrimidine, melting point: 211° C.

(76) 2-(3-ethoxycarbonylphenylamino)-4-methylamino-5-nitro-pyrimidine, melting point: 201–202° C.

(78) 2-[4-(2-tert.butoxycarbonylaminoethoxy)phenylamino]-4-methylamino-5-nitro-pyrimidine Carried out in the presence of N-ethyl-diisopropylamine, melting point: 205–207° C., $R_f$ value: 0.37 (silica gel; methylene chloride/methanol/conc. aqueous ammonia=20:1:0.1)

(85) 2-(4-butylphenylamino)-4-methylamino-5-nitro-pyrimidine, melting point: 207° C.

(86) 2-(4-trifluoromethoxyphenylamino)-4-methylamino-5-nitro-pyrimidine, melting point: 201° C.

(87) 2-(3-ethynylphenylamino)-4-methylamino-5-nitro-pyrimidine, melting point: 239° C.

(88) 2-[4-(ethoxycarbonylmethyl)phenylamino]-4-methylamino-5-nitro-pyrimidine, melting point: 226° C.

(89) 2-(1,2,3,4-tetrahydroquinolin-1-yl)-4-methylamino-5-nitro-pyrimidine, melting point: 138–140° C.

(90) 2-(pentafluorophenylamino)-4-methylamino-5-nitro-pyrimidine, melting point: 212–215° C.

(91) 2-(3-carboxyphenylamino)-4-methylamino-5-nitro-pyrimidine, melting point: >380° C. (decomp.), Mass spectrum: $M^+$=289

(92) 2-[(4-methylsulphonylaminophenyl)amino]-4-methylamino-5-nitro-pyrimidine, $R_f$ value: 0.78 (silica gel; cyclohexane/ethyl acetate=1:4), Mass spectrum: $M^+$=338

(95) 2-(3-azido-4-chlorophenylamino)-4-methylamino-5-nitro-pyrimidine, $R_f$ value: 0.42 (silica gel; cyclohexane/ethyl acetate=1:1)

(97) 2-(4-chloro-3-iodophenylamino)-4-methylamino-5-nitro-pyrimidine, melting point: 252–254° C.

EXAMPLE 2

2-(4-chlorophenylamino)-4-methylamino-5-amino-pyrimidine 3.0 g of 2-(4-chlorophenylamino)-4-methylamino-5-nitro-pyrimidine are hydrogenated in 300 ml of methanol and 150 ml of dimethylformamide in the presence of 1 g of platinum on charcoal (5% platinum) for one hour at a hydrogen pressure of 50 psi. The reaction mixture is filtered and the filtrate is evaporated to dryness in vacuo. The residue is combined with 40 ml water and stirred for 30 minutes. The solid is suction filtered, washed with water and dried.

Yield: 2.27 g (85% of theory), melting point: 188–190° C.

The following compounds are obtained analogously to Example 2:

(1) 2-(3,4-dichlorophenylamino)-4-methylamino-5-amino-pyrimidine, melting point: 225–227° C.

(2) 2-(3,4-dichlorophenylamino)-4-isopropylamino-5-amino-pyrimidine, melting point: 160° C.

(3) 2-(3,4-dichlorophenylamino)-4-butylamino-5-amino-pyrimidine, melting point: 144° C.

(4) 2-(3,4-dichlorophenylamino)-4-[3-(dimethylamino)propylamino]-5-amino-pyrimidine, melting point: 113–115° C.

(6) 2-(4-chloro-2-fluorophenylamino)-4-methylamino-5-amino-pyrimidine, melting point: 210° C.

(7) 2-(3,4-dichlorophenylamino)-4-(2-methoxyethylamino)-5-amino-pyrimidine, melting point: 177° C.

(8) 2-(4-tert.butylphenylamino)-4-methylamino-5-amino-pyrimidine, melting point: 213° C.

(9) 2-(3,4-dichlorophenylamino)-4-dimethylamino-5-amino-pyrimidine, $R_f$ value: 0.71 (silica gel; ethyl acetate/methanol=9:1)
(10) 2-(3,4-dichlorophenylamino)-4-ethylamino-5-amino-pyrimidine, melting point: 170° C.
(11) 2-(3,4-dichlorophenylamino)-4-[(2-dimethylaminoethyl)amino]-5-amino-pyrimidine, $R_f$ value: 0.35 (silica gel; ethyl acetate/methanol/conc. aqueous ammonia=9:1:1)
(12) 2-(2-chlorophenylamino)-4-methylamino-5-amino-pyrimidine, melting point: 236° C.
(13) 2-phenylamino-4-methylamino-5-amino-pyrimidine, melting point: 156° C.
(14) 2-(3-chlorophenylamino)-4-methylamino-5-amino-pyrimidine, melting point: 169° C.
(15) 2-(3,4-dimethylphenylamino)-4-methylamino-5-amino-pyrimidine, melting point: 172° C.
(16) 2-(5-indanylamino)-4-methylamino-5-amino-pyrimidine, melting point: 163° C.

EXAMPLE 3

2-(4-chlorophenylamino)-4-methylamino-5-formylamino-pyrimidine 200 mg of 2-(4-chlorophenylamino)-4-methylamino-5-amino-pyrimidine are refluxed in 5 ml of formic acid for 5 hours. The reaction mixture is evaporated to dryness and then the residue is stirred with 15 ml of water. The solid is suction filtered, washed with water, briefly boiled with 15 ml ethanol, cooled, suction filtered again, then washed with hot ethanol and dried.

Yield: 71 mg (34% of theory), melting point: 250–253° C.

The following compounds are obtained analogously to Example 3:
(1) 2-(3,4-dichlorophenylamino)-4-methylamino-5-formylamino-pyrimidine, melting point: 250–251° C.
(2) 2-(3,4-dichlorophenylamino)-4-methylamino-5-[(bis-methylsulphonyl)amino]-pyrimidine
Carried out with methanesulphonylchloride/pyridine, melting point: 226–228° C.
(3) 2-(3,4-dichlorophenylamino)-4-methylamino-5-methylsulphonylamino-pyrimidine
Carried out with methanesulphonylchloride/pyridine, melting point: 263–266° C.
(4) 2-(3,4-dichlorophenylamino)-4-methylamino-5-acetylamino-pyrimidine
Carried out with acetic anhydride/triethylamine, melting point: 267° C.
(7) 2-(4-chlorophenylamino)-4-[2-(acetylamino)ethylamino]-5-nitro-pyrimidine
Carried out with acetic anhydride/triethylamine, melting point: 224–226° C.
(8) 2-(4-chlorophenylamino)-4-[2-(methanesulphonylamino)ethylamino]-5-nitro-pyrimidine
Carried out with methanesulphonylchloride/triethylamine, melting point: 231–235° C.
(9) 2-(4-chlorophenylamino)-4-[3-(acetylamino)propylamino]-5-nitro-pyrimidine
Carried out with acetic anhydride/pyridine, $R_f$ value: 0.44 (silica gel; methylene chloride/methanol=9:1)
(10) 2-(4-chlorophenylamino)-4-[3-(methanesulphonylamino)propylamino]-5-nitro-pyrimidine
Carried out with methanesulphonylchloride/pyridine, $R_f$ value: 0.55 (silica gel; methylene chloride/methanol=9:1)
(11) 2-(4-chlorophenylamino)-4-[4-(acetylamino)butylamino]-5-nitro-pyrimidine,
Carried out with acetic anhydride/pyridine, $R_f$ value: 0.42 (silica gel; methylene chloride/methanol=9:1)
(12) 2-(4-chlorophenylamino)-4-[4-(methanesulphonylamino)butylamino]-5-nitro-pyrimidine
Carried out with acetic anhydride/pyridine, $R_f$ value: 0.56 (silica gel; methylene chloride/methanol=9:1)
(15) 2-(3-methylsulphonylaminomethyl-4-chloro-phenylamino)-4-methylamino-5-nitro-pyrimidine
Carried out with methanesulphonic acid chloride/triethylamine, melting point: 250° C.
(17) 2-(3,4-dichlorophenylamino)-4-methylamino-5-ethylsulphonylamino-pyrimidine
Carried out with ethylsulphonic acid chloride/pyridine, melting point: 239–241° C.
(18) 2-(3,4-dichlorophenylamino)-4-methylamino-5-isopropylsulphonylamino-pyrimidine
Carried out with isopropylsulphonic acid chloride/pyridine, melting point: 185–187° C.
(19) 2-(3,4-dichlorophenylamino)-4-methylamino-5-butylsulphonylamino-pyrimidine
Carried out with butylsulphonic acid chloride/pyridine, melting point: 190–192° C.
(20) 2-(3,4-dichlorophenylamino)-4-methylamino-5-phenylsulphonylamino-pyrimidine
Carried out with phenylsulphonic acid chloride/pyridine, melting point: 228–230° C.
(21) 2-(3,4-dichlorophenylamino)-4-methylamino-5-benzylsulphonylamino-pyrimidine
Carried out with benzylsulphonic acid chloride/pyridine, melting point: 233–235° C.
(22) 2-(3,4-dichlorophenylamino)-4-methylamino-5-dimethylsulphamoylamino-pyrimidine
Carried out with dimethylsulphamoylchloride/pyridine, $R_f$ value: 0.55 (silica gel; ethyl acetate/methanol=20:1)
(23) 2-(3,4-dichlorophenylamino)-4-methylamino-5-trifluoromethylsulphonylamino-pyrimidine
(24) 2-(3,4-dichlorophenylamino)-4-methylamino-5-propionylamino-pyrimidine
Carried out with propionic acid chloride/pyridine, $R_f$ value: 0.61 (silica gel; ethyl acetate/methanol/conc. aqueous ammonia=9:1:0.1)
(25) 2-(3,4-dichlorophenylamino)-4-methylamino-5-(dimethylphosphinylamino)-pyrimidine
Carried out with dimethylphosphinic acid chloride/pyridine, melting point: 258° C.
(26) 2-(3,4-dichlorophenylamino)-4-methylamino-5-(imidazolidin-2-on-1-yl)-pyrimidine
Carried out with 2-chloroethyl isocyanate/dimethylformamide and subsequent treatment with potassium tert. butoxide, melting point: 271° C., $R_f$ value: 0.17 (silica gel; ethyl acetate)
(27) 2-(3,4-dichlorophenylamino)-4-methylamino-5-isobutyrylamino-pyrimidine
Carried out with isobutyric acid chloride/pyridine, melting point: 284–286° C.
(28) 2-(3,4-dichlorophenylamino)-4-methylamino-5-butylcarbonylamino-pyrimidine
Carried out with valeric acid chloride/pyridine, melting point: 260–263° C.
(29) 2-(3,4-dichlorophenylamino)-4-methylamino-5-benzoylamino-pyrimidine
Carried out with benzoylchloride/pyridine, melting point: 265–267° C.
(30) 2-(3,4-dichlorophenylamino)-4-methylamino-5-morpholinocarbonylamino-pyrimidine Carried out with morpholinocarbonylchloride/pyridine, $R_f$ value: 0.42 (silica gel; methylene chloride/methanol/conc. aqueous ammonia=9:1:0.1))

(31) 2-(3,4-dichlorophenylamino)-4-methylamino-5-(2-carboxyethylcarbonylamino)-pyrimidine Carried out with succinic acid anhydride, melting point: 243° C.

(32) 2-(3,4-dichlorophenylamino)-4-methylamino-5-(1-imino-ethylamino)-pyrimidine Carried out with ethyl acetimidate/hydrochloride/triethylamine in tetrahydrofuran, melting point: 241° C.

(33) 2-(3,4-dichlorophenylamino)-4-methylamino-5-(tetrahydro-2(1H)-pyrimidinon-1-yl)-pyrimidine Carried out with 3-chloropropylisocyanate and subsequent treatment with potassium tert. butoxide, $R_f$ value: 0.23 (silica gel; ethyl acetate/methanol=4:1)

(34) 2-(3,4-dichlorophenylamino)-4-methylamino-5-(dimethylamino-methyleneimino)-pyrimidine Carried out with dimethylformamide-dimethylacetal, $R_f$ value: 0.72 (aluminium oxide; ethyl acetate/methanol=9:1)

(35) 2-(4-chloro-2-fluorophenylamino)-4-methylamino-5-(imidazolidin-2-on-1-yl)-pyrimidine Carried out with 2-chloroethyl isocyanate and subsequent treatment with potassium tert. butoxide, melting point: 249° C.

(36) 2-(4-chloro-2-fluorophenylamino)-4-methylamino-5-(N,N-dimethylcarbamoyl-amino)-pyrimidine Carried out with N,N-dimethylcarbamidic acid chloride/pyridine, melting point: 300° C.

(37) 2-(4-chloro-2-fluorophenylamino)-4-methylamino-5-(morpholinocarbonylamino)-pyrimidine Carried out with morpholinocarbonylchloride/pyridine, $R_f$ value: 0.34 (silica gel; ethyl acetate/methanol=9:1)

(38) 2-(3,4-dichlorophenylamino)-4-methylamino-5-phenoxycarbonylamino-pyrimidine Carried out with phenyl chloroformate/pyridine in tetrahydrofuran, melting point: 306° C.

(39) 2-(3,4-dichlorophenylamino)-4-methylamino-5-ethylaminocarbonylamino-pyrimidine Carried out with ethyl isocyanate, melting point: 333–335° C.

(40) 2-(3,4-dichlorophenylamino)-4-methylamino-5-aminocarbonylamino-pyrimidine

Carried out with potassium cyanate/acetic acid, $R_f$ value: 0.42 (Reversed Phase silica gel; Acetonitrile/water/trifluoroacetic acid=50:50:1)

(41) 2-(3,4-dichlorophenylamino)-4-methylamino-5-(N,N-dimethylcarbamoylamino)-pyrimidine Carried out with N,N-dimethylcarbamidic acid chloride/pyridine, melting point: 319–322° C.

(42) 2-(3,4-dichlorophenylamino)-4-methylamino-5-ethoxycarbonylamino-pyrimidine

Carried out with ethyl chloroformate/pyridine in tetrahydrofuran, Mass spectrum: $M^+$=355/357/359

(43) 2-(3,4-dichlorophenylamino)-4-methylamino-5-methoxycarbonylamino-pyrimidine Carried out with methyl chloroformate/pyridine in tetrahydrofuran, melting point: 303–305° C.

(44) 2-(3,4-dichlorophenylamino)-4-methylamino-5-isopropoxycarbonylamino-pyrimidine, melting point: 324–326° C.

(45) 2-(3,4-dichlorophenylamino)-4-methylamino-5-benzyloxycarbonylamino-pyrimidine, $R_f$ value: 0.60 (aluminium oxide; ethyl acetate/methanol=4:1)

(46) 2-(4-chloro-2-fluorophenylamino)-4-methylamino-5-acetylamino-pyrimidine, $R_f$ value: 0.50 (silica gel; methylene chloride/methanol=4:1)

(47) 2-(4-chloro-2-fluorophenylamino)-4-methylamino-5-[(bis-methanesulphonyl)amino]pyrimidine, melting point: 232–234° C.

(48) 2-(4-chloro-2-fluorophenylamino)-4-methylamino-5-methanesulphonylamino-pyrimidine, melting point: 204–206° C.

(49) 2-(3,4-dichlorophenylamino)-4-(2-methoxyethylamino)-5-(morpholinocarbonylamino)-pyrimidine, melting point: 182° C.

(53) 2-(3,4-dichlorophenylamino)-4-[(3-dimethylaminopropyl)amino]-5-(morpholinocarbonylamino)-pyrimidine, melting point: 240° C.

(54) 2-(3,4-dichlorophenylamino)-4-dimethylamino-5-(morpholinocarbonylamino)-pyrimidine, melting point: 340° C.

(55) 2-(3,4-dichlorophenylamino)-4-ethylamino-5-(morpholinocarbonylamino)-pyrimidine, $R_f$ value: 0.47 (silica gel; ethyl acetate/methanol/conc. aqueous ammonia=9:1:1)

(56) 2-(3,4-dichlorophenylamino)-4-[(2-dimethylaminoethyl)amino]-5-(morpholinocarbonylamino)-pyrimidine, $R_f$ value: 0.83 (silica gel; ethyl acetate/methanol/conc. aqueous ammonia=3:2:1)

(57) 2-(2-chlorophenylamino)-4-methylamino-5-(morpholinocarbonylamino)-pyrimidine, melting point: 264° C., $R_f$ value: 0.57 (silica gel; ethyl acetate/methanol/conc. aqueous ammonia=9:1:1)

(58) 2-phenylamino-4-methylamino-5-(morpholinocarbonylamino)-pyrimidine, melting point: 250° C.

(59) 2-(3-chlorophenylamino)-4-methylamino-5-(morpholinocarbonylamino)-pyrimidine, melting point: 295° C.

(60) 2-(4-chlorophenylamino)-4-methylamino-5-(morpholinocarbonylamino)-pyrimidine, melting point: 321° C.

(61) 2-(3,4-dimethylphenylamino)-4-methylamino-5-(morpholinocarbonylamino)-pyrimidine, $R_f$ value: 0.47 (silica gel; ethyl acetate/methanol/conc. aqueous ammonia=9:1:1)

(62) 2-(5-indanylamino)-4-methylamino-5-(morpholinocarbonylamino)-pyrimidine, $R_f$ value: 0.48 (silica gel; ethyl acetate/methanol/conc. aqueous ammonia=9:1:1), Mass spectrum: $M^+$=368

(63) 2-(4-tert.butylphenylamino)-4-methylamino-5-(morpholinocarbonylamino)-pyrimidine, $R_f$ value: 0.51 (silica gel; ethyl acetate/methanol/conc. aqueous ammonia=9:1:1), Mass spectrum: $(M+H)^+$=385

(64) 2-(3,4-dichlorophenylamino)-4-methylamino-5-(phenoxythiocarbonylamino)-pyrimidine, $R_f$ value: 0.78 (silica gel; ethyl acetate/methanol/conc. aqueous ammonia=9:1:1)

(65) 2-(3,4-dichlorophenylamino)-4-methylamino-5-[(ethoxycarbonylmethyl)aminocarbonylamino]-pyrimidine Carried out with ethyl isocyanatoacetate, melting point: 304° C.

(66) 2-(3,4-dichlorophenylamino)-4-methylamino-5-trifluoracetylamino-pyrimidine, melting point: 222° C.

(67) 2-(3,4-dichlorophenylamino)-4-methylamino-5-(imidazolidin-2,4-dion-3-yl)-pyrimidine Prepared from the compound of Example 3(65) by treating with sodium methoxide in methanol, melting point: 301° C.

EXAMPLE 4

2-(4-chlorophenylamino)-4-cyclopropylamino-5-nitro-pyrimidine 0.93 g of cyclopropylamine are added to 1 g of 2-(4-chlorophenylamino)-4-thiocyanato-5-nitro-pyrimidine in 10 ml dimethylformamide and stirred for 1½ hours at ambient temperature. 30 ml of water are added, the solid is suction filtered, washed with water and dried.

Yield: 0.81 g (82% of theory), melting point: 238–240° C.
The following compounds are obtained analogously to Example 4:
(1) 2-(4-chlorophenylamino)-4-propylamino-5-nitro-pyrimidine, melting point: 223–225° C.
(2) 2-(4-chlorophenylamino)-4-butylamino-5-nitro-pyrimidine, melting point: 190–192° C.
(3) 2-(4-chlorophenylamino)-4-ethylamino-5-nitro-pyrimidine, melting point: 222–225° C.
(4) 2-(4-chlorophenylamino)-4-isopropylamino-5-nitro-pyrimidine, melting point: 207–210° C.
(5) 2-(4-chlorophenylamino)-4-allylamino-5-nitro-pyrimidine, melting point: 185–187° C.
(6) 2-(4-chlorophenylamino)-4-propargylamino-5-nitro-pyrimidine, melting point: 190–192° C.
(7) 2-(3,4-dichlorophenylamino)-4-isopropylamino-5-nitro-pyrimidine, melting point: 226° C.
(8) 2-(3,4-dichlorophenylamino)-4-butylamino-5-nitro-pyrimidine, melting point: 156–157° C.
(9) 2-(3,4-dichlorophenylamino)-4-[3-(dimethylamino)propylamino]-5-nitro-pyrimidine, melting point: 168–170° C.
(10) 2-(3,4-dichlorophenylamino)-4-(2-hydroxyethylamino)-5-nitro-pyrimidine, melting point: 196° C.
(11) 2-(3,4-dichlorophenylamino)-4-(2-methoxyethylamino)-5-nitro-pyrimidine, melting point: 165° C.
(12) 2-(3,4-dichlorophenylamino)-4-[2-(dimethylamino)ethylamino]-5-nitro-pyrimidine, melting point: 175–176° C.
(13) 2-(3,4-dichlorophenylamino)-4-(2-morpholinoethylamino)-5-nitro-pyrimidine, melting point: 190° C.
(14) 2-(3,4-dichlorophenylamino)-4-[4-(dimethylamino)butylamino]-5-nitro-pyrimidine, melting point: 110° C.
(15) 2-(4-chlorophenylamino)-4-pyrrolidino-5-nitro-pyrimidine, melting point: 204–206° C.
(16) 2-(4-chlorophenylamino)-4-morpholino-5-nitro-pyrimidine, melting point: 218–220° C.
(17) 2-(4-chlorophenylamino)-4-(4-methylpiperazino)-5-nitro-pyrimidine, melting point: 178–180° C.
(18) 2-(4-chlorophenylamino)-4-diethylamino-5-nitro-pyrimidine, melting point: 173–175° C.
(19) 2-(4-chlorophenylamino)-4-(2-hydroxyethylamino)-5-nitro-pyrimidine, melting point: 226–228° C.
(20) 2-(4-chlorophenylamino)-4-(2-methoxyethylamino)-5-nitro-pyrimidine, melting point: 153–155° C.
(21) 2-(4-chlorophenylamino)-4-[2-(dimethylamino)ethylamino]-5-nitro-pyrimidine, melting point: 179–181° C.
(22) 2-(4-chlorophenylamino)-4-(2-aminoethylamino)-5-nitro-pyrimidine, $R_f$ value: 0.30 (silica gel; methylene chloride/methanol/conc. aqueous ammonia=9:1:0.1)
(23) 2-(4-chlorophenylamino)-4-benzylamino-5-nitro-pyrimidine, melting point: 212–215° C.
(24) 2-(4-chlorophenylamino)-4-(2-phenylethylamino)-5-nitro-pyrimidine, melting point: 210–212° C.
(25) 2-(4-chlorophenylamino)-4-(4-hydroxybutylamino)-5-nitro-pyrimidine, melting point: 178–182° C.
(26) 2-(4-chlorophenylamino)-4-piperazino-5-nitro-pyrimidine, $R_f$ value: 0.20 (silica gel; methylene chloride/methanol/conc. aqueous ammonia=9:1:0.1)
(27) 2-(4-chlorophenylamino)-4-(3-hydroxypropylamino)-5-nitro-pyrimidine, melting point: 190–194° C.
(28) 2-(4-chlorophenylamino)-4-(3-methoxypropylamino)-5-nitro-pyrimidine, melting point: 148–150° C.
(29) 2-(4-chlorophenylamino)-4-(2-cyanoethylamino)-5-nitro-pyrimidine, melting point: 203° C.
(30) 2-(4-chlorophenylamino)-4-[3-(dimethylamino)propylamino]-5-nitro-pyrimidine, melting point: 148–150° C.
(31) 2-(4-chlorophenylamino)-4-[4-(dimethylamino)butylamino]-5-nitro-pyrimidine, melting point: 131–132° C.
(32) 2-(4-chlorophenylamino)-4-(3-aminopropylamino)-5-nitro-pyrimidine, $R_f$ value: 0.28 (silica gel; methylene chloride/methanol/conc. aqueous ammonia=9:1:0.1)
(33) 2-(4-chlorophenylamino)-4-(4-aminobutylamino)-5-nitro-pyrimidine, $R_f$ value: 0.30 (silica gel; methylene chloride/methanol/conc. aqueous ammonia=9:1:0.1)
(34) 2-(4-chlorophenylamino)-4-(ethoxycarbonylmethylamino)-5-nitro-pyrimidine, melting point: 202–204° C.
(35) 2-(4-chlorophenylamino)-4-[2-(ethoxycarbonyl)ethylamino]-5-nitro-pyrimidine, melting point: 163–165° C.
(36) 2-(4-chlorophenylamino)-4-[3-(ethoxycarbonyl)propylamino]-5-nitro-pyrimidine, melting point: 133–135° C.
(42) 2-(3,4-dichlorophenylamino)-4-(2,2,2-trifluoroethylamino)-5-nitro-pyrimidine, melting point: 183–185° C.
(43) 2-(3,4-dichlorophenylamino)-4-(1-azeridinyl)-5-nitro-pyrimidine, melting point: 220–223° C.
(44) 2-(3,4-dichlorophenylamino)-4-(1-aziridinyl)-5-nitro-pyrimidine, melting point: 198–200° C.
(45) 2-(3,4-dichlorophenylamino)-4-ethylamino-5-nitro-pyrimidine, melting point: 225° C.
(46) 2-(3,4-dichlorophenylamino)-4-[(2-ethoxycarbonylethyl)amino]-5-nitro-pyrimidine, melting point: 137° C.
(47) 2-(3,4-dichlorophenylamino)-4-(2-chloroethylamino)-5-nitro-pyrimidine, melting point: 272–274° C.

EXAMPLE 5

2-(3-aminomethyl-4-chloro-phenylamino)-4-methylamino-5-nitro-pyrimidine-dihydrochloride 10 ml of 4N hydrochloric acid are added to 2 g of 2-[3-(tert.butyloxycarbonylaminomethyl)-4-chloro-phenylamino]-4-methylamino-5-nitro-pyrimidine in 60 ml of ethyl acetate and the mixture is refluxed for 2 hours. After cooling it is suction filtered and washed several times with ethyl acetate.

Yield: 560 mg (30% of theory), mp: >350° C., $R_f$ value: 0.63 (silica gel; ethyl acetate/methanol=9:1)

The following compounds are obtained analogously to Example 5:
(1) 2-(4-aminomethyl-phenylamino)-4-methylamino-5-nitro-pyrimidine-dihydrochloride, melting point: >340° C., $R_f$ value: 0.53 (Reversed Phase silica gel; acetonitrile/water=1:1 with 1% trifluoroacetic acid)
(2) 2-[4-(2-aminoethyl)-phenylamino]-4-methylamino-5-nitro-pyrimidine, melting point: 220–223° C.
(3) 2-[4-(2-aminoethoxy)-phenylamino]-4-methylamino-5-nitro-pyrimidine-dihydrochloride×1 H$_2$O, melting point: 280–282° C.

| Calc.: | C | 39.50 | H | 5.10 | N | 21.26 | Cl | 17.04 |
|---|---|---|---|---|---|---|---|---|
| Found: |  | 39.47 |  | 5.03 |  | 21.12 |  | 17.50 |

(4) 2-[3-(2-aminoethoxy)-phenylamino]-4-methylamino-5-nitro-pyrimidine-dihydrochloride, melting point: 270° C.

EXAMPLE 6

2-(2,3,4,5-tetrahydro-1H-3-benzazepin-7-yl-amino)-4-methylamino-5-nitro-pyrimidine 650 mg of 2-(3-trifluoroacetyl-2,3,4,5-tetrahydro-1H-3-benzazepin-7-yl-amino)-4-methylamino-5-nitro-pyrimidine, 20 ml tetrahydrofuran, 10 ml water and 3.2 ml of 1N sodium hydroxide solution are stirred for 2 hours at ambient temperature and then the reaction mixture is combined with 100 ml of water. The solid precipitated is suction filtered and dried.

Yield: 420 mg (83% of theory), melting point: 222° C.

EXAMPLE 7

2-(4-chlorophenylamino)-4-(carboxymethylamino)-5-nitro-pyrimidine 30 ml of 1N sodium hydroxide solution and 20 ml of water are added to 4.5 g of 2-(4-chlorophenylamino)-4-(ethoxycarbonylmethylamino)-5-nitro-pyrimidine in 40 ml of tetrahydrofuran and the mixture is stirred for 3 hours at ambient temperature. Then 31 ml of 1N hydrochloric acid are added with stirring, the solid precipitated is suction filtered, washed with water and dried.

Yield: 4.14 g (100% of theory), melting point: >300° C., $R_f$ value: 0.36 (silica gel; methylene chloride/methanol=9:1)

The following compounds are obtained analogously to Example 7:
(1) 2-(4-chlorophenylamino)-4-(2-carboxyethylamino)-5-nitro-pyrimidine, melting point: >300° C.
$R_f$ value: 0.40 (silica gel; methylene chloride/methanol=9:1)
(2) 2-(4-chlorophenylamino)-4-(3-carboxypropylamino)-5-nitro-pyrimidine, melting point: 258–260° C.
(3) 2-[4-(2-carboxyethyl)phenylamino]-4-methylamino-5-nitro-pyrimidine, melting point: 260° C.
(4) 2-[4-(carboxymethyl)phenylamino]-4-methylamino-5-nitro-pyrimidine, melting point: 286° C.
(5) 2-(3,4-dichlorophenylamino)-4-[(2-carboxyethyl)amino]-5-nitro-pyrimidine, $R_f$ value: 0.16 (silica gel; cyclohexane/ethyl acetate/methanol=7:2:1)

EXAMPLE 8

2-(3,4-dichlorophenylamino)-4-methylamino-5-(N-methyl-methylsulphonylamino)-pyrimidine 0.034 ml of methyl iodide are added to 200 mg of 2-(3,4-dichlorophenylamino)-4-methylamino-5-methylsulphonylamino-pyrimidine and 80 mg of potassium carbonate in 3 ml of dimethylformamide and stirred overnight at ambient temperature. The reaction mixture is poured onto 20 ml of water, the solid is suction filtered and dried. Yield: 180 mg (87% of theory), melting point: 196° C., $R_f$ value: 0.50 (silica gel; ethyl acetate/methanol=9:1)

The following compounds are obtained analogously to Example 8:
(1) 2-[N-(3,4-dichlorophenyl)-N-methylamino]-4-methylamino-5-(3-methyl-imidazolidin-2-on-1-yl)-pyrimidine
Prepared from the compound of Example 3(26) with sodium hydride/methyl iodide, melting point: 203° C.
(2) 2-[N-(3,4-dichlorophenyl)-N-methylamino]-4-methylamino-5-(imidazolidin-2-on-1-yl)-pyrimidine
Prepared from the compound of Example 3(26) with sodium hydride/methyl iodide, $R_f$ value: 0.33 (silica gel; ethyl acetate/methanol=9:1)
(3) 2-(3,4-dichlorophenyl)-4-methylamino-5-[N-(morpholinocarbonyl)-N-methylamino]-pyrimidine
Prepared from the compound of Example 3(30) with sodium hydride/methyl iodide, melting point: 227° C.

EXAMPLE 9

N-[2-(3,4-dichlorophenylamino)-4-methylamino-pyrimidine-5-yl]-2,2,2-trichloroacetamidine 1.62 ml of methyl 2,2,2-trichloroacetimidate are added to 3.45 g of 2-(3,4-dichlorophenylamino)-4-methylamino-5-amino-pyrimidine in 50 ml glacial acetic acid and stirred overnight at ambient temperature. Then the solid is suction filtered, washed with glacial acetic acid and dried.

Yield: 4.35 g (84% of theory), $R_f$ value: 0.83 (silica gel; ethyl acetate/methanol=9:1), Mass spectrum: M+=426/428/430/432/434

EXAMPLE 10

2-(4-methylsulphinylphenylamino)-4-methylamino-5-nitro-pyrimidine and 2-(4-methylsulphonylphenylamino)-4-methylamino-5-nitro-pyrimidine 1.23 g of m-chloroperoxybenzoic acid (content: 57–86%) are added to 1.0 g of 2-(4-methylsulphenylphenylamino)-4-methylamino-5-nitropyrimidine in 30 ml of methylene chloride and stirred overnight at ambient temperature. The reaction mixture is separated by chromatography through a silica gel column with methylene chloride/methanol (50:1).

a) 2-(4-methylsulphinylphenylamino)-4-methylamino-5-nitropyrimidine

Yield: 28 mg (2.6% of theory), melting point: 288° C., $R_f$ value: 0.60 (silica gel; methylene chloride/methanol=9:1)

b) 2-(4-methylsulphonylphenylamino)-4-methylamino-5-nitropyrimidine

Yield: 25 mg (2.2% of theory), melting point: 323° C., $R_f$ value: 0.80 (silica gel; methylene chloride/methanol=9:1)

EXAMPLE 11

2-(3,4-dichlorophenylamino)-4-methylamino-5-(pyrrolidinocarbonylamino)-pyrimidine 250 mg of 2-(3,4-dichlorophenylamino)-4-methylamino-5-(phenoxycarbonylamino)-pyrimidine and 2.5 ml of pyrrolidine are stirred for 1 hour at ambient temperature. The reaction mixture is added to 20 ml of water, the solid is suction filtered, stirred with methanol, suction filtered again and dried.

Yield: 110 mg (46% of theory), melting point: >350° C., $R_f$ value: 0.31 (silica gel; ethyl acetate/methanol/conc. aqueous ammonia=9:1:1)

The following compounds are obtained analogously to Example 11:
(1) 2-(3,4-dichlorophenylamino)-4-methylamino-5-(piperidinocarbonylamino)-pyrimidine melting point: 329° C.
(2) 2-(3,4-dichlorophenylamino)-4-methylamino-5-(4-methylpiperazinocarbonylamino)-pyrimidine, melting point: 327° C.
(3) 2-(3,4-dichlorophenylamino)-4-methylamino-5-[[bis-(2-methoxyethyl)amino]-carbonylamino]-pyrimidine, melting point: 162° C., $R_f$ value: 0.41 (silica gel; ethyl acetate/methanol/conc. aqueous ammonia=9:1:1)
(4) 2-(3,4-dichlorophenylamino)-4-methylamino-5-(hexamethyleneiminocarbonylamino)-pyrimidine, $R_f$ value: 0.54 (silica gel; ethyl acetate/methanol/conc. aqueous ammonia=9:1:1), Mass spectrum: $M^+$=408/410/412
(5) 2-(3,4-dichlorophenylamino)-4-methylamino-5-(diethylaminocarbonylamino)-pyrimidine, melting point: 329° C.
(6) 2-(3,4-dichlorophenylamino)-4-methylamino-5-(piperazinocarbonylamino)-pyrimidine, melting point: 324° C.
(7) 2-(3,4-dichlorophenylamino)-4-methylamino-5-(4-acetylpiperazinocarbonylamino)-pyrimidine, melting point: 301° C.
(8) 2-(3,4-dichlorophenylamino)-4-methylamino-5-[[N-methyl-(2-hydroxyethyl)-amino]carbonylamino]-pyrimidine, melting point: 325° C.
(9) 2-(3,4-dichlorophenylamino)-4-methylamino-5-(methylaminocarbonylamino)-pyrimidine, melting point: 328° C.
(10) 2-(3,4-dichlorophenylamino)-4-methylamino-5-[[N-methyl-(2-dimethylamino-ethyl)amino]carbonylamino]-pyrimidine, melting point: 326° C.
(11) 2-(3,4-dichlorophenylamino)-4-methylamino-5-[[N-methyl-(3-dimethylaminopropyl)amino]carbonylamino]-pyrimidine, melting point: 324° C.
(12) 2-(3,4-dichlorophenylamino)-4-methylamino-5-(morpholinothiocarbonylamino)-pyrimidine, $R_f$ value: 0.15 (silica gel; ethyl acetate), Mass spectrum: $M^+$=410/412/414

EXAMPLE 12

2-(3,4-dichlorophenylamino)-4-methylamino-5-(3-methyl-imidazolidin-2-on-1-yl)-pyrimidine 300 mg of 2-(3,4-dichlorophenylamino)-4-methylamino-5-[[N-methyl-(2-hydroxyethyl)-amino]carbonylamino]-pyrimidine and 205 mg of triphenylphosphine in 6 ml of tetrahydrofuran are combined with 0.13 ml of diethyl azodicarboxylate and stirred overnight at ambient temperature. The reaction mixture is purified by chromatography through a silica gel column with ethyl acetate/methanol/conc. aqueous ammonia (19:1:0.5).

Yield: 86 mg (30% of theory), melting point: 350° C.

EXAMPLE 13

2-(3,4-dichlorophenylamino)-4-methylamino-5-(pyrrol-1-yl)-pyrimidine 0.5 g of 2-(3,4-dichlorophenylamino)-4-methylamino-5-amino-pyrimidine and 0.15 ml o 2,5-dimethoxy-tetrahydrofuran are refluxed in 25 ml of glacial acetic acid for 3 hours and then stirred for 2½ days at ambient temperature. The solid is suction filtered and purified by chromatography through a silica gel column.

Yield: 0.34 g (56% of theory), $R_f$ value: 0.66 (silica gel; methylene chloride/methanol=9:1)

The compounds according to the invention may be administered orally, transdermally, intrathecally, by inhalation or parenterally and occur as active ingredients in conventional preparations, for example in compositions which consist essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 1 and 5000, preferably between 10 and 1000, most preferably between 10–100 mg/dose for oral administration, and between 0.001 and 100, preferably between 0.1 and 10 mg/dose for intravenous or intramuscular administration. For inhalation, according to the invention, solutions containing 0.01 to 1.0, preferably 0.1 to 0.5% active substance are suitable. For administration by inhalation the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 and 5000 mg, preferably 100–1000 mg per adult.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed therein. The mixture is cooled to 38° C. and poured into slightly chilled suppository moulds.

The invention claimed is:
1. A compound of formula I:

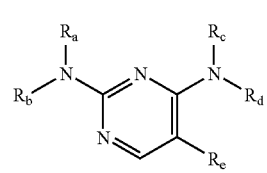

(I)

$R_a$ and $R_d$ each independently of one another represent a hydrogen atom or a methyl group, $R_b$ denotes a phenyl group substituted by one or two fluorine or chlorine atoms, $R_c$ a methyl, ethyl or propyl group, which may be terminally substituted by a dimethylamino group, $R_e$ denotes a nitro amino group, formylamino, $C_{1-4}$-alkylcarbonylamino, cyclopropylcarbonylamino, phenylcarbonylamino, $C_{1-3}$-alkoxycarbonylamino, benzyloxycarbonylamino, phenyloxycarbonylamino, $C_{1-4}$-alkylsulphonylamino, N-methyl-methylsulphonylamino, di(methylsulphonyl)amino, phenylsulphonylamino, benzylsulphonylamino, trifluoroacetylamino, dimethylaminosulphonylamino, dimethylphosphinylamino, 1-iminoethylamino, 1-imino-2,2,2-trichloroethylamino or N',N'-dimethyl-N-formamidino group, a pyrrolidinocarbonylamino, piperidinocarbonylamino, homopiperidinocarbonylamino, morpholinocarbonylamino, piperazinocarbonylamino, 4-methylpiperazinocarbonylamino or 4-acetylpiperazinocarbonylamino group which may be substituted by a methyl group at the carbonylamino moiety in each case, a morpholinothiocarbonylamino group, a $R_7NR_8$—CO—$NR_6$-group wherein:
$R_6$ denotes a hydrogen atom or a methyl group, and $R_7$ and $R_8$ in each case independently of one another represent hydrogen atoms or $C_{1-3}$-alkyl groups, while the alkyl groups may be terminally substituted by a hydroxy, methoxy, dimethylamino or $C_{1-2}$-alkoxycarbonyl group, or
$R_6$ and $R_7$ together denote a n-$C_{2-3}$-alkylene group, and $R_8$ denotes a hydrogen atom or a methyl group, an imidazolidine-2,4-dion-3-yl-group, a carboxy, $C_{1-2}$-alkoxycarbonyl or cyano group, an aminosulphonyl, methylaminosulphonyl or dimethylaminosulphonyl group, a 1-pyrrolyl or 5-tetrazolyl group, or a tautomer, stereoisomer or salt thereof.

2. A compound according to claim 1, wherein:

$R_e$ denotes a nitro, acetylamino, trifluoroacetylamino, methylsulphonamino or amino group, or a urea group of formula $R_7NR_8$—CX—$NR_6$, wherein $R_6$ denotes a hydrogen atom or an alkyl group, $R_7$ and $R_8$, which may be identical or different, denotes hydrogen atoms or alkyl groups optionally substituted by hydroxy, methoxy or dimethylamino, or $R_6$ and $R_7$ together denote an n-$C_{2-3}$-alkylene group, and $R_8$ denotes a hydrogen atom or an alkyl group optionally substituted by hydroxy, methoxy or dimethylamino, or $R_7$ and $R_8$ taken together denote a $C_{4-8}$-alkylenediyl group, while one or two non-adjacent $CH_2$ groups may be replaced by —O—, —S or —$NR_{23}$—, wherein $R_{23}$ denotes a hydrogen atom, a $C_{1-3}$-alkyl group or $C_{1-3}$-alkanoyl group, and X denotes O or S, or a tautomer, stereoisomer or salt thereof.

3. A selected from:

2-(4-chloroanilino)-4-methylamino-5-nitro-pyrimidine;
2-(3,4-dichloroanilino)-4-methylamino-5-amino-pyrimidine;
2-(3,4-dichloroanilino)-4-methylamino-5-methylsulphonamino-pyrimidine;
2-(3,4-dichloroanilino)-4-(3-dimethylaminopropyl)-amino-5-nitro-pyrimidine;
2-(3,4-dichloroanilino)-4-methylamino-5-acetamido-pyrimidine;
2-(3,4-dichloroanilino)-4-methylamino-5-(N-methyl-N-methylsulphonylamino)-pyrimidine;
2-(3,4-dichloroanilino)-4-methylamino-5-(2-oxo-imidazolidin-1-yl)-pyrimidine;
2-(3,4-dichloroanilino)-4-methylamino-5-(morpholin-1-ylcarbonylamino)-pyrimidine;
2-(3,4-dichloroanilino)-4-methylamino-5-($N_2,N_2$-dimethylureido)-pyrimidine;
2-[N-(3,4-dichlorophenyl)-N-methylamino]-4-methylamino-5-(2-oxo-imidazolidin-1-yl)-pyrimidine;
2-(3,4-dichloroanilino)-4-methylamino-5-(2-oxo-tetrahydropyrimidin-1-yl)-pyrimidine;
2-(3,4-dichloroanilino)-4-methylamino-5-ureido-pyrimidine; 2-(3,4-dichloroanilino)-4-dimethylamino-5-(morpholin-1-ylcarbonylamino)-pyrimidine;
2-(3,4-dichloroanilino)-4-ethylamino-5-(morpholin-1-ylcarbonylamino)-pyrimidine;
2-(3-chloroanilino)-4-methylamino-5-(morpholin-1-ylcarbonylamino)-pyrimidine;
2-(3,4-dichloroanilino)-4-methylamino-5-(pyrrolidin-1-ylcarbonylamino)-pyrimidine;
2-(3,4-dichloroanilino)-4-methylamino-5-(4-methylpiperazin-1-ylcarbonylamino)-pyrimidine;
2-(3,4-dichloroanilino)-4-methylamino-5-[$N^2,N^2$-di-(2-methoxyethyl)-ureido]-pyrimidine;
2-(3,4-dichloroanilino)-4-methylamino-5-(azepanyl-1-carbonylamino)-pyrimidine;
2-(3,4-dichloroanilino)-4-methylamino-5-($N_2,N_2$-diethylureido)-pyrimidine;
2-(3,4-dichloroanilino)-4-methylamino-5-(piperazin-1-ylcarbonylamino)-pyrimidine;
2-(3,4-dichloroanilino)-4-methylamino-5-(4-acetylpiperazin-1-ylcarbonylamino)-pyrimidine;
2-(3,4-dichloroanilino)-4-methylamino-5-[$N^2$-methyl-$N_2$-(2-hydroxyethyl)-ureido]-pyrimidine;
2-(3,4-dichloroanilino)-4-methylamino-5-(morpholin-1-ylthiocarbonylamino)-pyrimidine;
2-(3,4-dichloroanilino)-4-methylamino-5-(2,2,2-trifluoroacetamido)-pyrimidine;
2-(3,4-dichloroanilino)-4-methylamino-5-[$N_2$-methyl-$N^2$-(2-dimethylaminoethyl)-ureido]-pyrimidine;
2-(3,4-dichloroanilino)-4-methylamino-5-[$N_2$-methyl-$N_2$-(3-dimethylaminopropyl)-ureido]-pyrimidine;
and the salts thereof.

4. A physiological acceptable salt of a compound of formula (I) according to claim 1.

5. A method of inhibiting the formation of amyloid-β-peptide in cells in-vitro and/or inhibiting the release of amyloid-β-peptide from cells in-vitro comprising treating said cells with an effective amount of a compound of formula (I) according to claim 1.

6. A pharmaceutical composition comprising one or more compounds according to claim 1 and one or more inert pharmaceutical carriers.

7. A pharmaceutical composition according to claim 6, in the form of a tablet, coated tablet or capsule.

* * * * *